(12) United States Patent
Seeberger et al.

(10) Patent No.: US 6,579,725 B1
(45) Date of Patent: Jun. 17, 2003

(54) LINKERS FOR SYNTHESIS OF OLIGOSACCHARIDES ON SOLID SUPPORTS

(75) Inventors: Peter H. Seeberger, Cambridge, MA (US); Rodrigo B. Andrade, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/518,102

(22) Filed: Mar. 3, 2000

Related U.S. Application Data

(60) Provisional application No. 60/122,930, filed on Mar. 5, 1999.

(51) Int. Cl.[7] ........................ G01N 33/543; C07C 31/34

(52) U.S. Cl. ........................ 436/518; 568/841; 568/852; 568/857

(58) Field of Search ........................ 436/518; 585/610; 260/464; 568/841, 852, 857

(56) References Cited

U.S. PATENT DOCUMENTS

| | | | | |
|---|---|---|---|---|
| 4,041,061 A | * | 8/1977 | Buck ........................ | 260/464 |
| 5,489,678 A | | 2/1996 | Fodor et al. ................ | 536/22.1 |
| 5,527,681 A | | 6/1996 | Holmes ........................ | 435/6 |
| 5,550,215 A | | 8/1996 | Holmes ........................ | 530/334 |
| 5,635,612 A | | 6/1997 | Kahne ........................ | 536/18.5 |
| 5,744,101 A | | 4/1998 | Fodor et al. ................ | 422/131 |
| 5,753,788 A | | 5/1998 | Fodor et al. ................ | 536/22.1 |
| 5,770,456 A | | 6/1998 | Holmes ........................ | 436/518 |
| 5,889,165 A | | 3/1999 | Fodor et al. ................ | 536/22.1 |

FOREIGN PATENT DOCUMENTS

| | | |
|---|---|---|
| DE | 19621 177 A1 | 11/1997 |
| EP | 0937696 A1 | 8/1999 |
| EP | 985 662 A2 | 3/2000 |
| WO | WO 95/28640 | 10/1995 |
| WO | WO 97/20855 | 6/1997 |
| WO | WO 97/35202 | 9/1997 |
| WO | WO 98/08799 | 3/1998 |
| WO | WO 98/22487 | 5/1998 |
| WO | WO 98/29386 | 7/1998 |
| WO | WO 98/38197 | 9/1998 |
| WO | WO 98/45231 | 10/1998 |
| WO | WO 98/53813 | 12/1998 |
| WO | WO 99/15510 | 4/1999 |
| WO | WO 99/19332 | 4/1999 |
| WO | WO 99/39207 | 8/1999 |
| WO | WO 99/47498 | 9/1999 |
| WO | WO 99/64032 | 12/1999 |
| WO | WO 00/05197 | 2/2000 |
| WO | WO 00/07966 | 2/2000 |
| WO | WO 00/20112 | 4/2000 |
| WO | WO 00/21658 | 4/2000 |

OTHER PUBLICATIONS

Nicolaou et al., Nature, vol. 387, May 15, 1997, pp. 268–272.*

Tolstikov et al., Tetrahedron Letters, No. 12, pp 1857–1858, 1978.*

Schafer et al , Tetrahedron, vol. 18, No. 22, pp 3299–3308, 1982.*

Raederstorff et al., The Journal of organic Chemistry, vol. 52, No. 12, pp. 2337–2346, Jun. 1987.*

Andrade, Rodrigo B. et al., "Solid–Phase Oligosaccharide Synthesis: Preparation of Complex Structures Using a Novel Linker and Different Glycosylating Agents", Organic Letters 1(11): 1811–1814 (1999).

Hayashi, Nobuyuki et al., "The Biomimetic Construction of Fused Cyclic Polyethers", Tetrahedron 53(37): 12425–12468 (1997).

Jahn, Ullrich et al., "Towards a Tandem–Radical Macrocyclization–Transannular Cyclization Approach to Steroids: Transannular Cyclizations of a Macrocyclic Core", Tetrahedron Letters 36(49): 8921–8924 (1995).

Miura, Katsukiyo et al., "Highly Stereoselective Intramolecular Addition of a Hydroxyl Group to Vinylsilanes via 1,2–Silyl Migration", J. Org. Chem. 62: 8292–8293 (1997).

Raederstorff, Daniel et al., "Biosynthetic Studies of Marine Lipids. 11. Synthesis, Biosynthesis, and Absolute Configuration of the Internally Branched Demospongic Acid, 22–Methyl–5,9–Octacosadienoic Acid", Journal of Organic Chemistry 52(12): 2337–2346 (Jun. 12, 1987).

(List continued on next page.)

*Primary Examiner*—Padmashri Ponnaluri
(74) *Attorney, Agent, or Firm*—Dana M. Gordon; Foley Hoag LLP

(57) ABSTRACT

The present invention relates to versatile linkers for tethering a molecule to a solid support, e.g., for tethering a monomer, oligomer or polymer to a solid support, which are stable to a wide range of reaction conditions, but can be cleaved under well-defined conditions, thereby liberating the molecule from the solid support. Preferably, the linkers are used to tether to the solid support unprotected, partially-protected or fully-protected monosaccharides or oligosaccharides, or unprotected, partially-protected or fully-protected glycoconjugates. The linkers of the present invention may be used to tether to solid supports building blocks useful in the assembly of libraries of other types of small molecules. The present invention also relates to a molecule or plurality of molecules tethered to the solid support via a linker or linkers of the present invention. The present invention also relates to processes for synthesizing molecules, e.g., monomers, oligomers or polymers, on a solid support, wherein a starting material in the synthesis of the molecule, intermediates in the synthesis of the molecule, and the molecule itself are tethered to the solid support during the process via one of the linkers of the present invention. In certain processes of the present invention, the molecule is liberated from the solid support by cleavage of the linker of the present invention.

24 Claims, 11 Drawing Sheets

OTHER PUBLICATIONS

International Search Report Completed on Apr. 19, 2001 and Mailed on May 4, 2001.

Arya, P. and Ben, N. R.; Angew. Chem. Int. Ed. Engl. 36 (12): 1280–1282 (1997).

Boons et al.; "Vinyl Glycosides Oligosaccharide Synthesis: A Strategy for the Preparation of Trisaccharide Libraries Based on Latent–Active Glycosylation **", Angew. Chem. Int. Ed. Engl. 35 (23/24) : 2845–2847 (1996).

Ding et al.; "Synthesis and Bilogical Activity of Oligosaccharide Libraries", Glycoimmunology, Edited by A. Alavi and J. S. Axford; Plenum Press New York, (1965); pp. 261–269.

Frechet, M. J. and Schuerch, C. "Solid–Phase Synthesis of Oligosaccharides III. Preparation of Some Derivatives of Di– and Tri–Saccharides Via a Simple Alcoholysis Reaction", Carbohydr. Res. 22 : 399–412 (1972).

Fraser–Reid et al. ; "n–Pentenyl Glycosides in Organic Chemistry: A Contemporary Example of Serendipity", Synlett pp. 927–942 ( Dec. 1992 ).

Izumi, M. and Ichikawa, Y. "Combinatorial Synthesis of Oligosaccharide Library of 2.6–Dideoxysugars", Tetrahedron Letters 39 : 2079–2082 (1998).

Johnson et al.; "Vinyl Glycosides in Oligosaccharide Synthesis (Part 5)[1]: A Latent–Active Glycosylation Strategy for the Preparation of Branched Trisaccharide Libraries" Tetrahedron Letters 39 : 9801–9804 (1998).

Liang et al.; "Parallel Synthesis and Screening of a Solid Phase Carbohydrate Library", Science, 274 : 1520–1522 (Nov. 29, 1996).

Nicolaou, K. C. et al.; "Solid and Solution Phase Synthesis and Biological Evaluation of Combinatorial Sarcodictyin Libraries", J. Am. Chem. Soc. 120 : 10814–10826 (1998).

Nicolaou, K.C. et al.; "Solid–Phase Synthesis of Oligosaccharides: Construction of a Dodecasaccharide**", Angew. Chem. Int. Ed. 37 (11) : 1559–1561 (1998).

Osborn and Khan; "Recent Developments in Polymer Supported Syntheses of Oligosaccharides and Glycopeptides", Tetrahedron 55 : 1807–1850 (1999).

Rademann, J. and Schmidt, R. R. ; "A New Method for the Solid Phase Synthesis of Oligosaccharides[1]", Tetrahedron Letters 37 (23) : 3989–3990 (1996).

Rodebaugh et al. ; "Polymer–Supported Oligosaccharides via n–Pentenyl Glycosides : Methodology for a Carbohydrate Library [1]", J. Org. Chem. 62 : 5660–5661 (1997).

Scheffler, G. and Schmidt * R. R. "Glycosylation Reactions with a (4–Alkoxypentadienyl)oxy Leaving Group Linking the Glycosyl Donor and the Acceptor Moiety", J. Org. Chem. 64 : 1319–1325 (1999).

Schweizer, F. and Hindsgaul, O. "Combinatorial Synthesis of Carbohydrates", Current Opinion in Chemical Biology 3 (3) : 291–298 (Jun. 1999).

Sofia, M.J. et al. "Carbohydrate–Based Small–Molecule Scaffolds for the Construction of Universal Pharmacophore Mapping Libraries", J. Org. Chem. 63: 2802–2803 ( 1998).

Wang and Hindsgaul ; "Combinatorial Carbohydrate Chemistry", Glycoimmunology 2, Edited by Axford; Plenum Press, New York, pp. 219–236 (1998).

Wunberg et al.; "Carbohydrates as Multifunctional Chiral Scaffolds in Combinatorial Synthesis", Angew. Chem. Int. Ed. 37 (18) : 2503–2505 (1998).

* cited by examiner

LINKERS FOR SYNTHESIS OF OLIGOSACCHARIDES ON SOLID SUPPORTS

RELATED APPLICATIONS

This application claims the benefit of priority to U.S. Provisional Patent Application Ser. No. 60/122,930, filed Mar. 5, 1999.

BACKGROUND OF THE INVENTION

Nucleic acids, proteins and polysaccharides are three major classes of biopolymers. While the first two systems are principally linear assemblies, polysaccharides are structurally more complex. This structural and stereochemical diversity results in a rich content of "information" in relatively small molecules. Nature further "leverages" the structural versatility of polysaccharides by their covalent attachment (i.e., "conjugation") to other biomolecules such as isoprenoids, fatty acids, neutral lipids, peptides or proteins. Oligosaccharides in the form of glycoconjugates mediate a variety of events including inflammation, immunological response, metastasis and fertilization. Cell surface carbohydrates act as biological markers for various tumors and as binding sites for other substances including pathogens.

Moreover, many physiologically important recognition phenomena involving carbohydrates have been discovered in recent years. Lectins, proteins which contain carbohydrate recognition domains, have been identified. Prominent members of the calcium dependent (C-type) lectin family (Drickamer, K. Curr. Opin. Struct. Biol. 1993, 3, 393) are the selectins which play a crucial role in leukocyte recruitment in inflammation. Bevilacqua, M. P.; Nelson, R. M. J. Clin. Invest. 1993, 91, 379. Members of the C-type lectin superfamily have been described on NK cells and Ly-49, NKR-P1 and NKG2 constitute group V of C-type lectins. While many lectins have been purified and cloned, their ligands have not been identified due to the heterogeneous nature of carbohydrates.

The recognition that interactions between proteins and carbohydrates are involved in a wide array of biological recognition events, including fertilization, molecular targeting, intercellular recognition, and viral, bacterial and fungal pathogenesis, underscores the importance of carbohyrates in biological systems. It is now widely appreciated that the oligosaccharide portions of glycoproteins and glycolipids mediate certain recognition events between cells, between cells and ligands, between cells and the extracellular matrix, and between cells and pathogens. See, e.g., U.S. Pat. No. 4,916,219 (describing oligosaccharides with heparin-like anticomplement activity).

These recognition phenomena may be inhibited by oligosaccharides having the same sugar sequence and stereochemistry found on the active portion of a glycoprotein or glycolipid involved in the recognition phenomena. The oligosaccharides are believed to compete with the glycoproteins and glycolipids for binding sites on the relevant receptor(s). For example, the disaccharide galactosyl-β-1-4-N-acetylglucosamine is believed to be one component of the glycoproteins which interact with receptors in the plasma membrane of liver cells. Thus, to the extent that they compete with moieties for cellular binding sites, oligosaccharides and other saccharide compositions have the potential to open new horizons in pharmacology, diagnosis, and therapeutics.

The growing appreciation of the key roles of oligosaccharides and glycoconjugates in fundamental life sustaining processes has stimulated a need for access to usable quantities of these materials. Glycoconjugates are difficult to isolate in homogeneous form from living cells since they exist as microheterogeneous mixtures. The purification of these compounds, when possible, is at best tedious and generally provides only very small amounts of the compounds. The travails associated with isolation of oligo- and poly-saccharides and glycoconjugates from natural sources present a major opportunity for the development and exploitation of chemical synthesis. See, e.g., U.S. Pat. Nos. 4,656,133; 5,308,460; 5,514,784; and 5,854,391 (describing representative means of glycosylating saccharides and peptides).

Intense work is ongoing on the further development of the use of biologically-active oligosaccharides within a number of different fields, including novel diagnostics and blood typing reagents; highly specific materials for affinity chromatography; cell specific agglutination reagents; targeting of drugs; monoclonal antibodies, e.g., against cancer-associated reagents; as an alternative to antibiotics, based on the inhibition with specific oligosaccharides of the attachment of bacteria and viruses to cell surfaces; and stimulation of the growth of plants and protection of them against pathogens. Additionally, a considerable future market is envisaged for fine chemicals based on biologically-active carbohydrates.

As stated above, due to the difficulties associated with purification of glycoconjugates and oligosaccharides from natural sources, chemical synthesis may be the only way to procure sufficient amounts of these structures for detailed biochemical and biophysical studies. Additionally, combinatorial carbohydrate libraries hold great potential for the identification of carbohydrate-based ligands to cellular receptors. Identification of these molecules will open many new avenues for the development of diagnostic tools and therapeutic agents.

The invention of solid phase peptide synthesis by Merrifield 35 years ago dramatically influenced the strategy for the synthesis of these biopolymers. The preparation of structurally defined oligopeptides (Atherton, E.; Sheppard, R. C. Solid phase peptide synthesis: A practical approach; IRL Press at Oxford University Press: Oxford, England, 1989, pp 203) and oligonucleotides (Caruthers, M. H. Science 1985, 230, 281) has benefited greatly from the feasibility of conducting their assembly on various polymer supports. The advantages of solid matrix-based synthesis, in terms of allowing for an excess of reagents to be used and in the facilitation of purification are now well appreciated. However, the level of complexity associated with the synthesis of an oligosaccharide on a polymer support dwarfs that associated with the other two classes of repeating biooligomers. First, the need to differentiate similar functional groups (hydroxyl or amino) in oligosaccharide construction is much greater than the corresponding needs in the synthesis of oligopeptides or oligonucleotides. Furthermore, in these latter two cases, there is no stereoselection associated with construction of the repeating amide or phosphate bonds. In contrast, each glycosidic bond to be fashioned in a growing oligosaccharide ensemble constitutes a new locus of stereogenicity.

Combinatorial chemistry has been used in the synthesis of large numbers of structurally distinct molecules in a time and resource-efficient manner. Peptide, oligonucleotide, and small molecule libraries have been prepared and screened against receptors or enzymes to identify high-affinity ligands or potent inhibitors. These combinatorial libraries have provided large numbers of compounds to be screened against many targets for biological activity. Every pharmaceutical company now devotes a major effort to the area of combinatorial chemistry in order to develop new lead compounds in a rapid fashion.

The development of protocols for the solid support synthesis of oligosaccharides and glycopeptides requires solutions to several problems. Of course, considerable thought must be addressed to the nature of the support material. The availability of methods for attachment of the carbohydrate from either its "reducing" or "non-reducing" end would be advantageous. Also, selection of a linker which is stable during the synthesis, but can be cleaved easily when appropriate, is critical. A protecting group strategy that allows for high flexibility is desirable. Most important is the matter of stereospecific and high yielding coupling reactions.

Combinatorial carbohydrate libraries hold a tremendous potential with regard to therapeutic applications. The key role complex oligosaccharides play in biological processes such as inflammation, immune response, cancer and fertilization makes them highly attractive therapeutic targets. The ability to create true oligosaccharide libraries has the potential to trigger a revolution in the area of biopharmaceuticals.

The generation of combinatorial carbohydrate libraries will facilitate the rapid identification of ligands to many carbohydrate binding proteins which are involved in a variety of important biological events including inflammation (Giannis, A. *Angew. Chem. Int. Ed. Engl.* 1994, 33, 178), immune response (Ryan, C. A. *Proc. Natl. Acad. Sci. U.S.A.* 1994, 91, 1) and metastasis (Feizi, T. *Curr. Opin. Struct. Biol.* 1993, 3, 701). Analogs of ligands can help to define important lectin-ligand interactions. Non-natural ligands can be powerful inhibitors of carbohydrate-protein binding and will facilitate the study of cascade-like events involving such interactions. Furthermore, inhibitors of carbohydrate-lectin binding are potential candidates for a variety of therapeutic applications.

Moreover, the development of an automated oligosaccharide synthesizer holds great potential to influence glycobiology just as the peptide synthesizer impacted protein research. A reliable strategy for the solid support synthesis of oligosaccharides depends to a great extent on the choice of the linker which is used to anchor the first building block to the polymeric matrix.

SUMMARY OF THE INVENTION

A set of versatile linkers is described which are stable to a wide range of reaction conditions but can be cleaved in several ways to produce free oligosaccharides, fully-protected oligosaccharide building blocks and novel glycoconjugates. Furthermore, these linkers may be used to attach to solid supports building blocks useful in the assembly of libraries of other types of small molecules.

In certain embodiments, the present invention relates to versatile linkers for tethering a molecule to a solid support, e.g., for tethering a monomer, oligomer or polymer to a solid support, which are stable to a wide range of reaction conditions, but can be cleaved under well-defined conditions, thereby liberating said molecule from the solid support. In preferred embodiments, the linkers of the present invention are used to tether to the solid support unprotected, partially-protected or fully-protected monosaccharides or oligosaccharides, or unprotected, partially-protected or fully-protected glycoconjugates. In other embodiments, the linkers of the present invention may be used to tether to solid supports building blocks useful in the assembly of libraries of other types of small molecules. In certain embodiments, the present invention relates to a molecule or plurality of molecules tethered to the solid support via a linker or linkers of the present invention.

In certain embodiments, the present invention relates to processes for synthesizing molecules, e.g., monomers, oligomers or polymers, on a solid support, wherein a starting material in the synthesis of said molecule, intermediates in the synthesis of said molecule, and said molecule itself are tethered to the solid support during the process via one of the linkers of the present invention. In certain processes of the present invention, the molecule is liberated from the solid support by cleavage of the linker of the present invention.

The invention described herein is expected to enable the automated synthesis of oligosaccharides and glycoconjugates in much the same fashion that peptides and oligonucleotides are currently assembled. The ability to synthesize defined biologically important glycoconjugates will be far reaching with many direct applications to biomedical questions. Opportunities for the application of the present invention include the development of automated oligosaccharide synthesis machines.

DETAILED DESCRIPTION OF THE INVENTION

Figure 1:
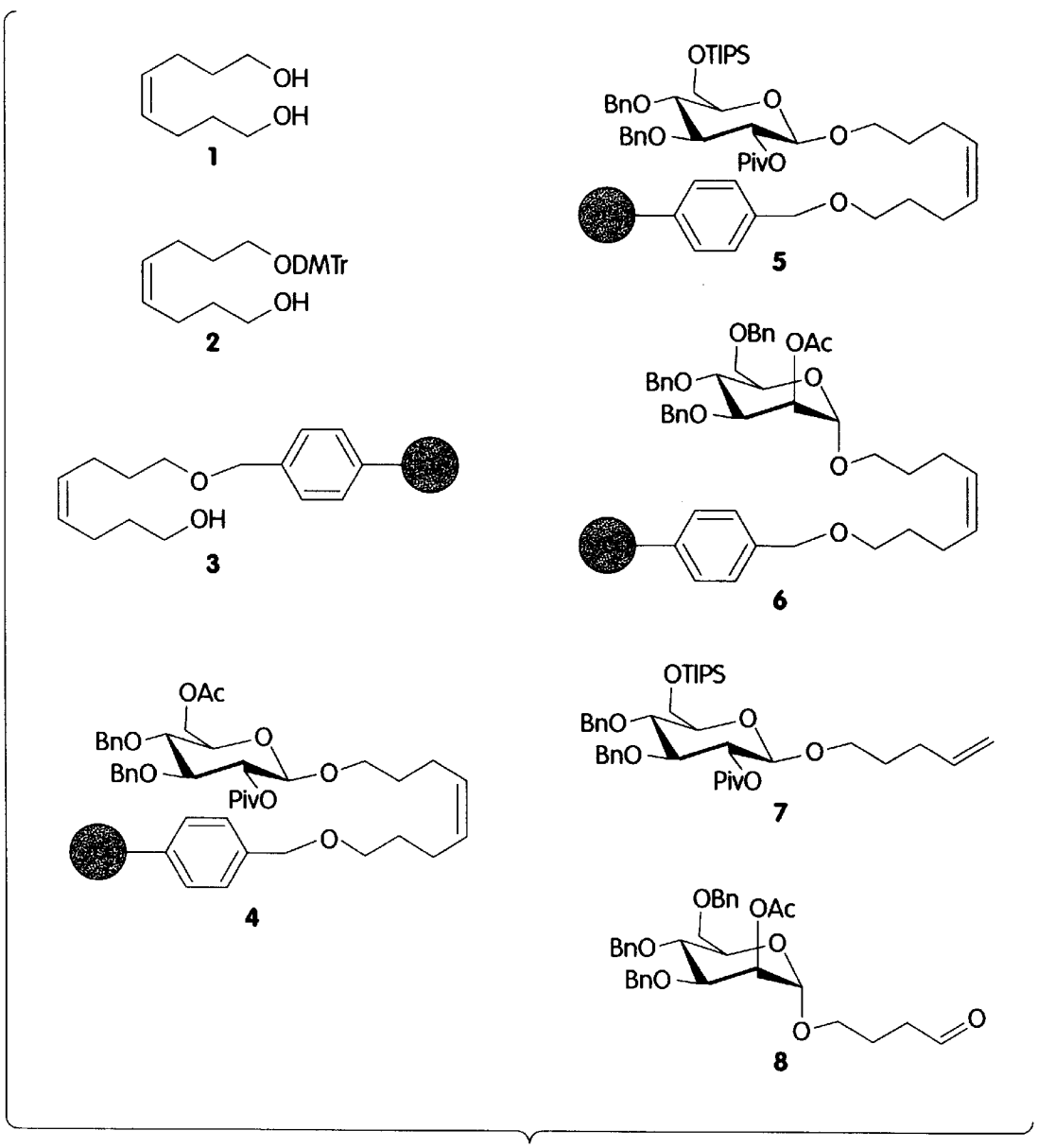
FIG. 1 depicts the structures of compounds 1–8 from Examples 1–8.
Figure 2:
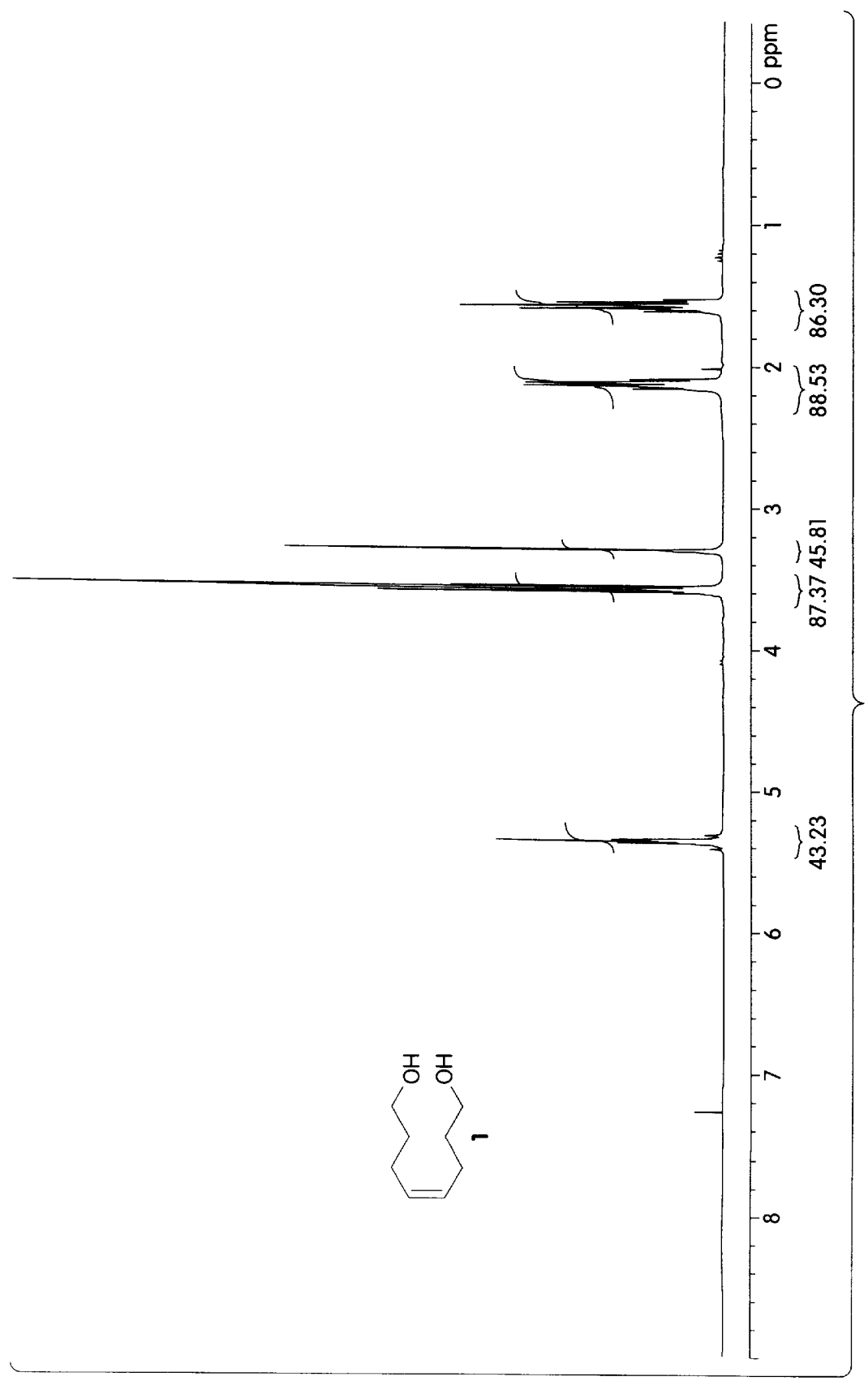
FIG. 2 depicts the $^1$H NMR spectrum of compound 1 from Example 1.
Figure 3:
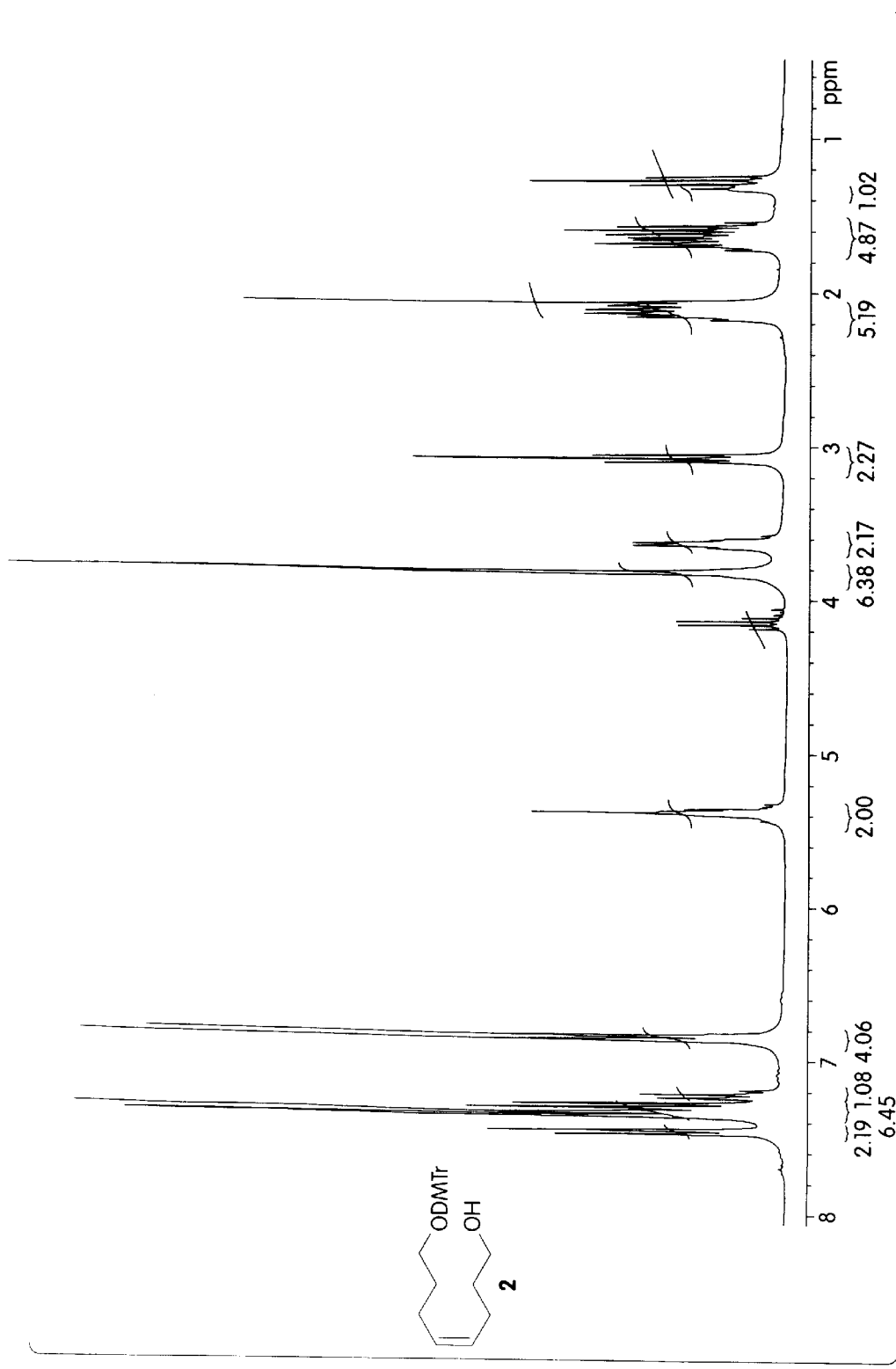
FIG. 3 depicts the $^1$H NMR spectrum of compound 2 from Example 2.
Figure 4:
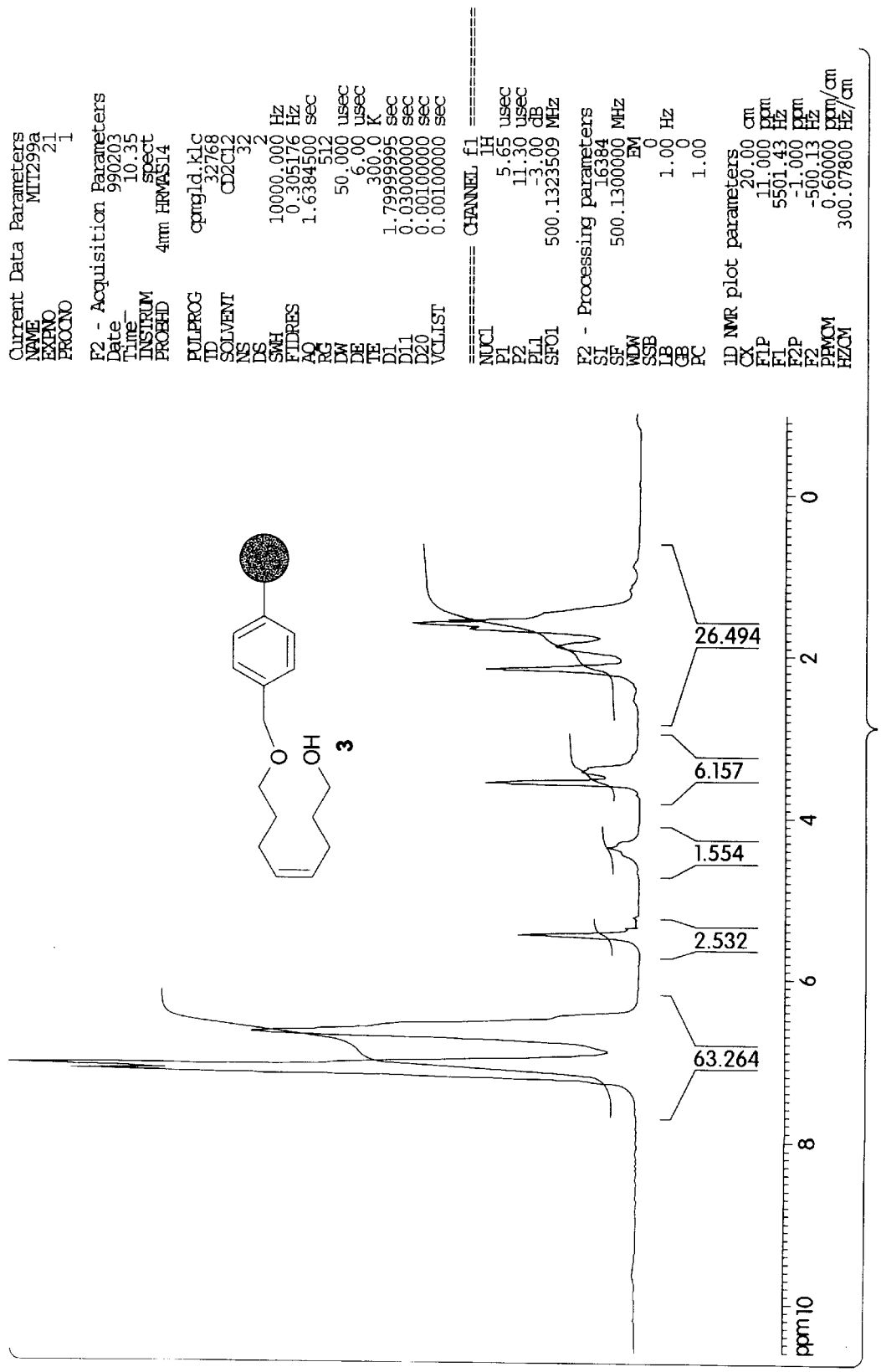
FIG. 4 depicts the $^1$H NMR spectrum of compound 3 from Example 3.
Figure 5:
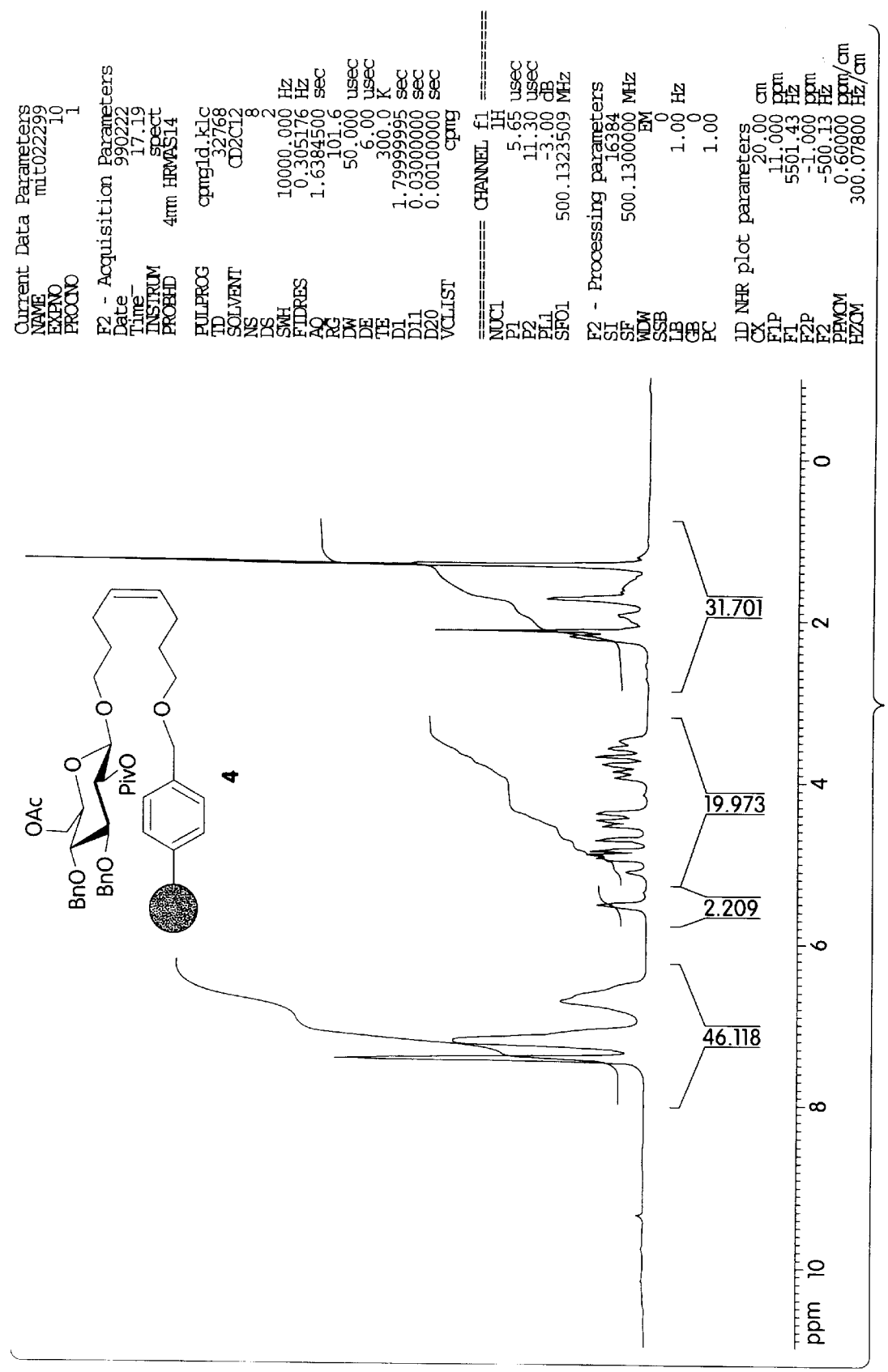
FIG. 5 depicts the $^1$H NMR spectrum of compound 4 from Example 4.
Figure 6:
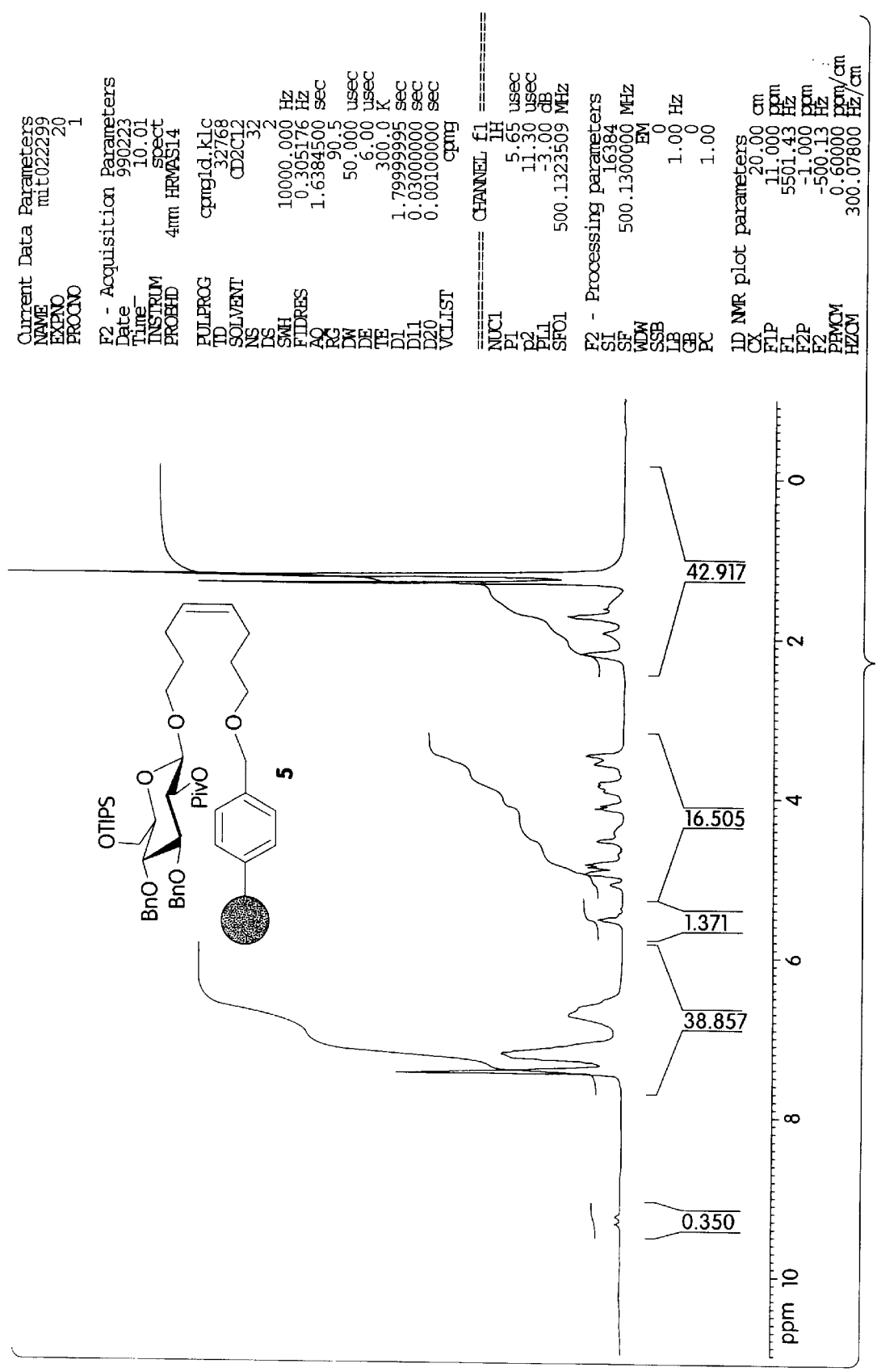
FIG. 6 depicts the $^1$H NMR spectrum of compound 5 from Example 5.
Figure 7:
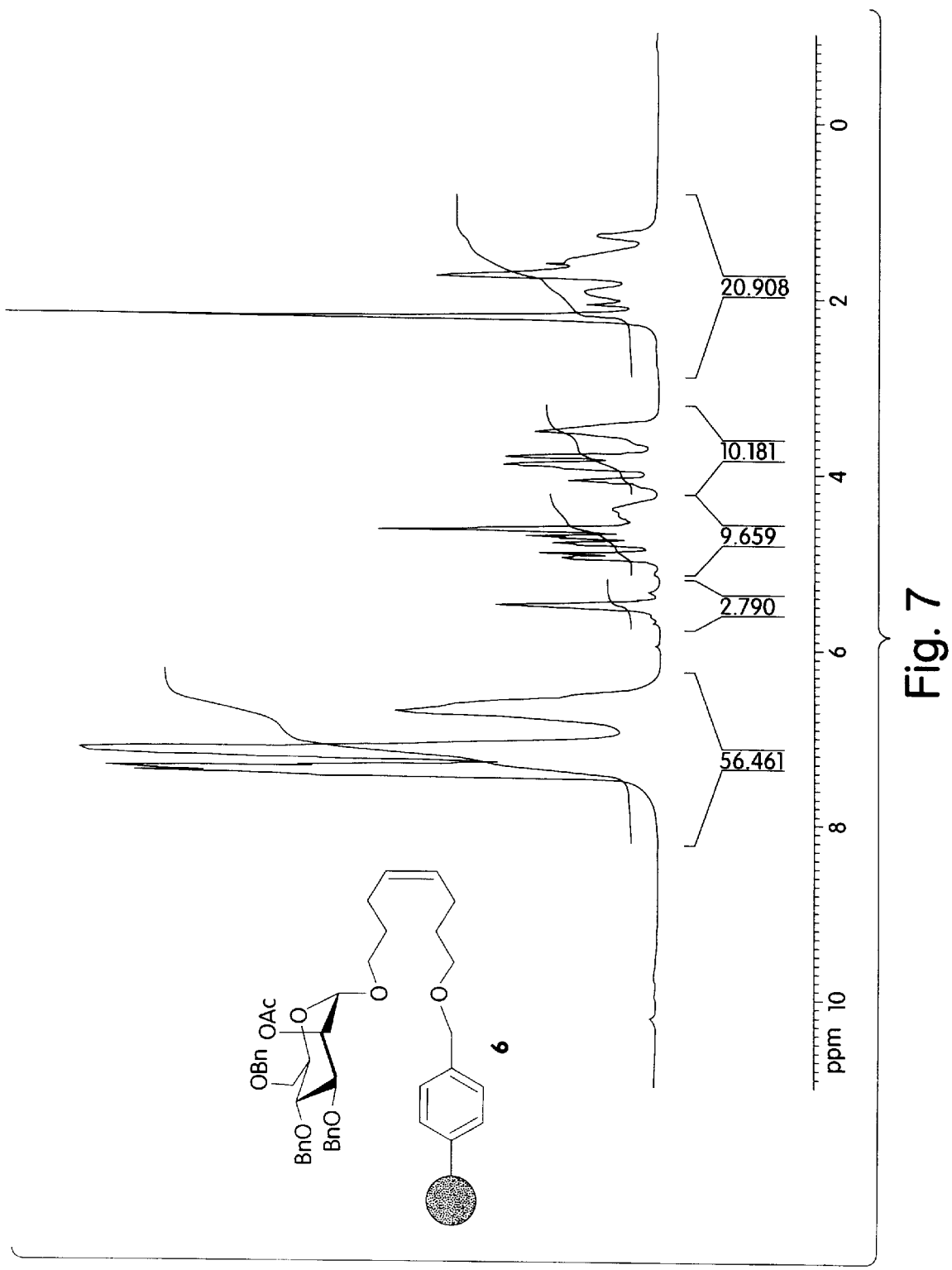
FIG. 7 depicts the $^1$H NMR spectrum of compound 6 from Example 6.
Figure 8:
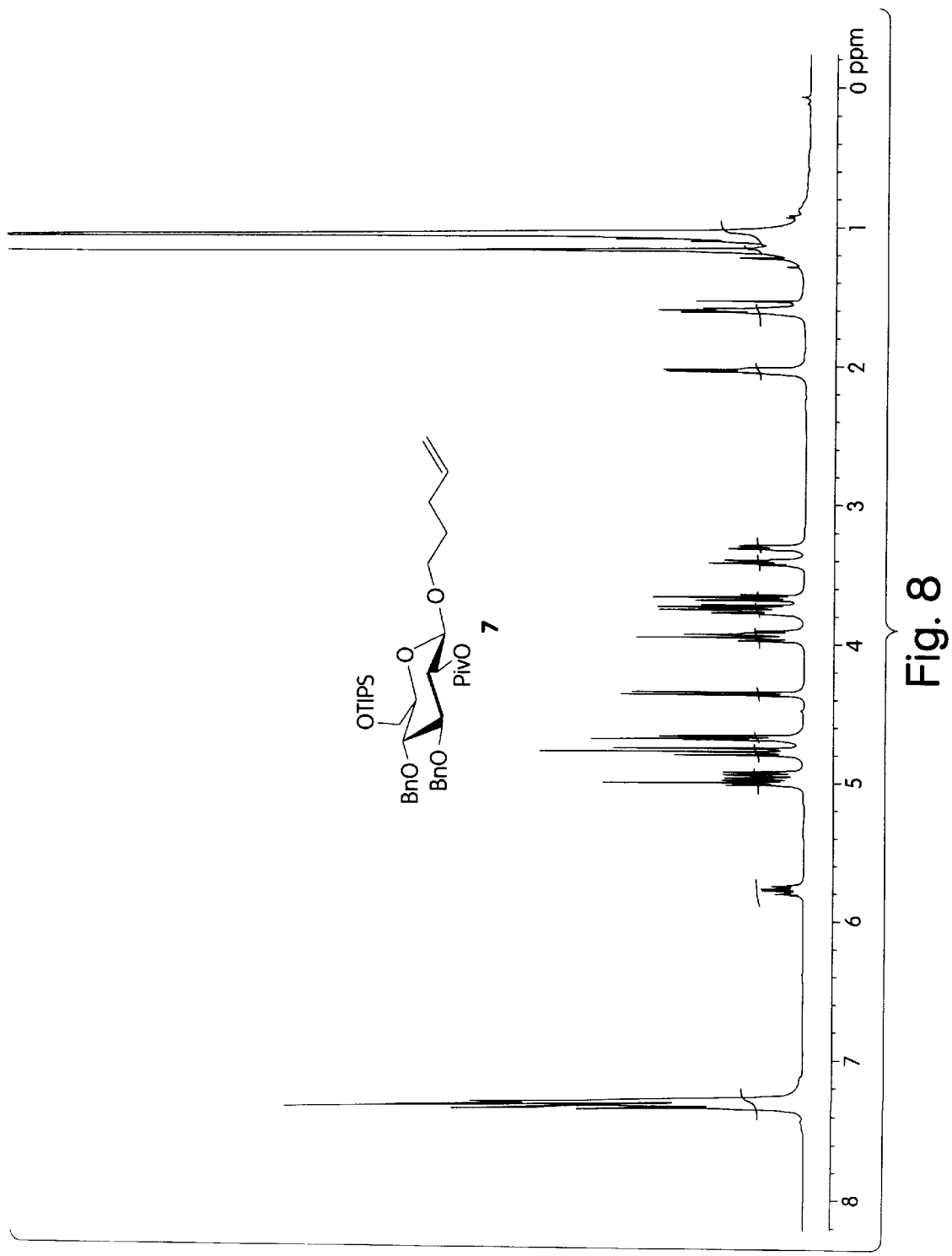
FIG. 8 depicts the $^1$H NMR spectrum of compound 7 from Example 7.
Figure 9:
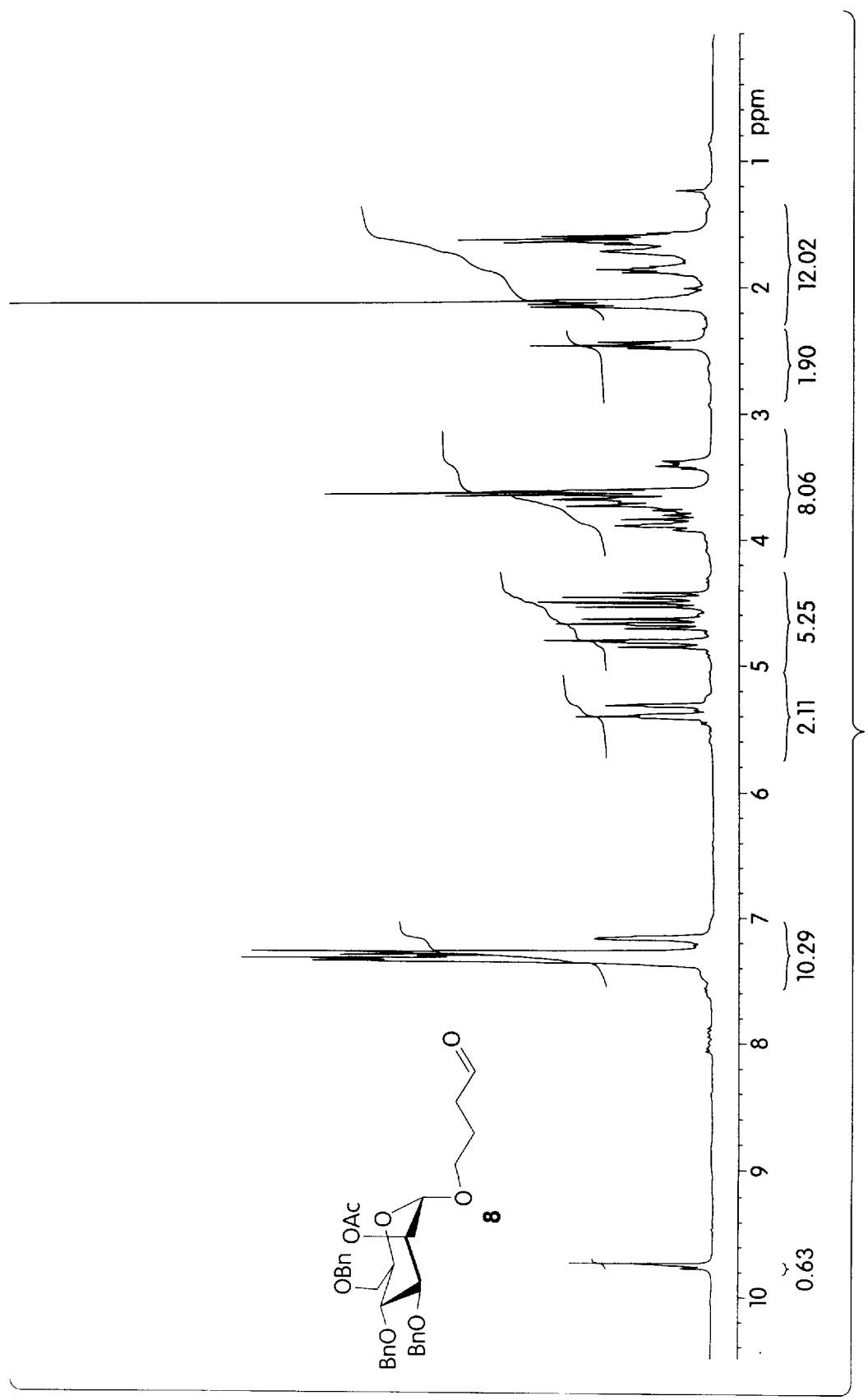
FIG. 9 depicts the $^1$H NMR spectrum of compound 8 from Example 8.
Figure 10A:
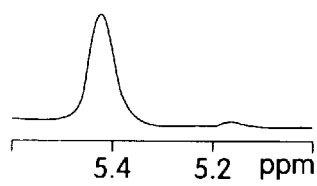
FIGS. 10*a–d* depicts HR-MAS NMR spectra of compounds 3 (spectrum a), 4 (spectrum b), 13 (spectrum c), and 10 (spectrum d) from Example 9.
Figure 10B:
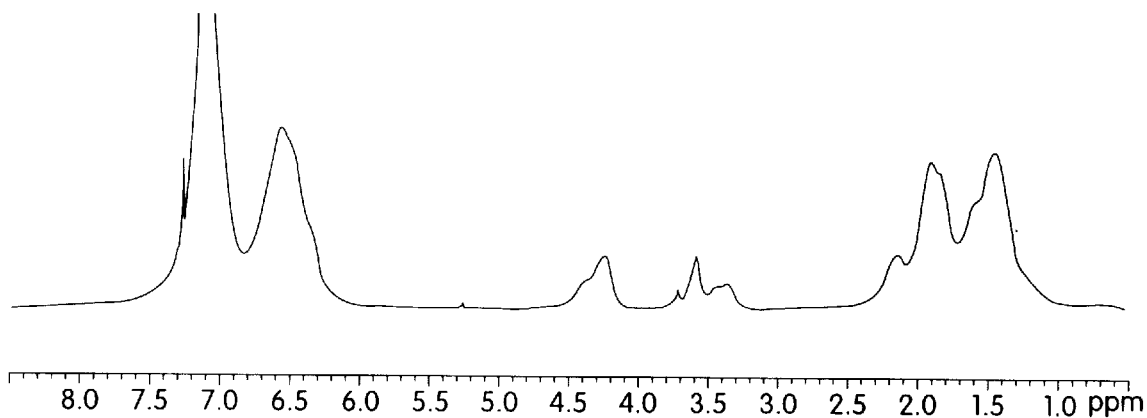
Figure 10C:
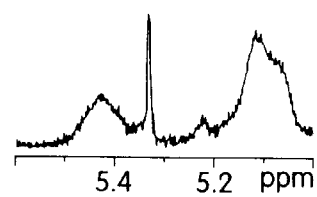
Figure 10D:
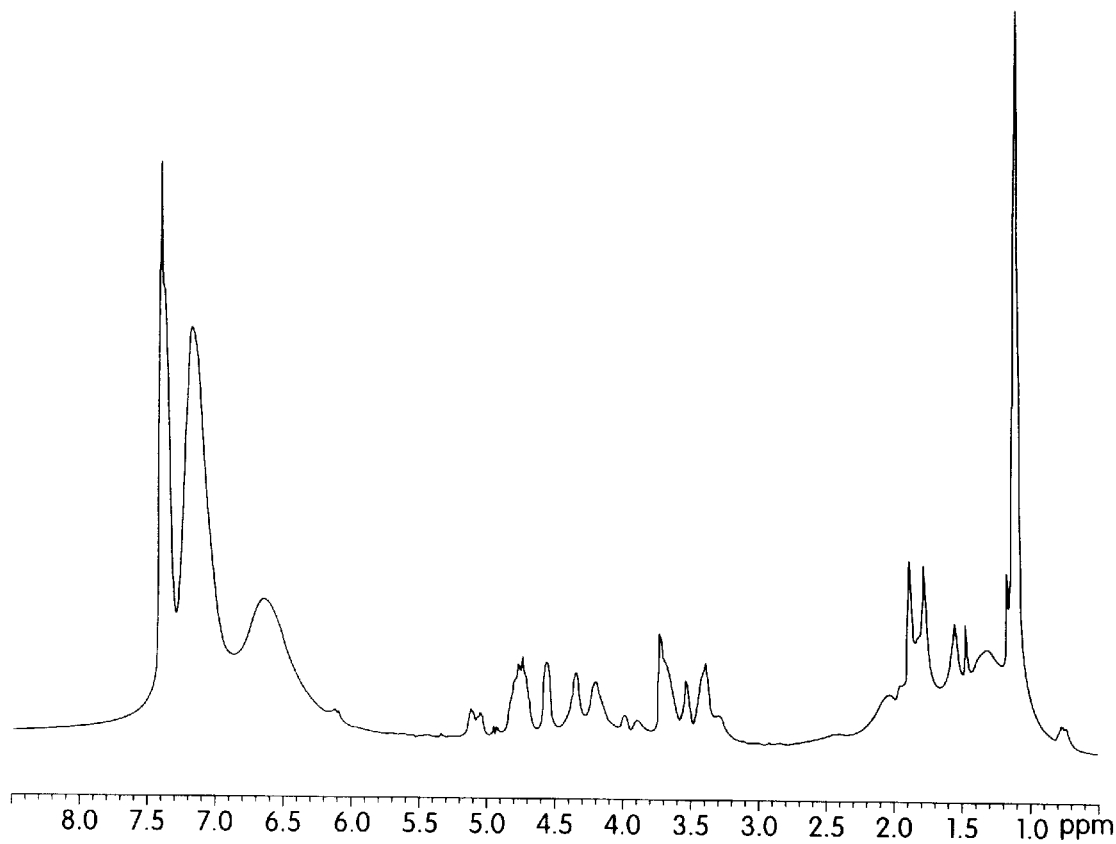

Novel, versatile linkers are described which are stable to a wide range of reaction conditions, but can be cleaved in several ways to provide free oligosaccharides, fully-protected oligosaccharide building blocks and glycoconjugates. Furthermore, the linkers may be used to attach to solid supports building blocks for the assembly of small molecule libraries.

The chemistry outlined below is a key element in a general scheme directed at the automated synthesis of oligosaccharides and glycoconjugates much in the same fashion that peptides and oligonucleotides are currently assembled. The ability to synthesize defined biologically relevant glycoconjugates has many direct applications to biomedical questions.

Polymeric resins equipped with linkers of the present invention can be marketed for use in combinatorial chemistry, and as a key elements in the solid-phase synthesis of oligosaccharides and combinatorial libraries of oligosaccharides.

The linker which is used to attach the first sugar, or other building block, to the solid support can be viewed as a solid support-containing protecting group on the first building block. The chemical nature of this linker significantly influences the overall synthetic strategy as it informs the protecting group strategies and the reaction conditions that may be employed in the synthetic strategy. Complete stability of the linker during the synthesis and selective cleavage in high yield at the end of the synthesis are highly desirable. Linkers used to date for solid support oligosaccharide synthesis include silyl ethers, thioethers, succinyl esters and nitrobenzyl ethers. All of these linkers impose limitations upon the scope of reagents and protecting groups that may be employed during the synthesis, thus underscoring the need for new linker designs.

The present invention relates to new linkers for the attachment of molecules, and libraries thereof, to solid supports. In certain embodiments, the molecules are saccharides, oligosaccharides, and/or polysaccharides wherein the individual saccharide residues attached directly to the linkers are attached via their anomeric carbons, and the linkers have the characteristic that at least one set of conditions for releasing the saccharides, oligosaccharides, and/or polysaccharides from the solid support provides saccharides, oligosaccharides, and/or polysaccharides wherein the residues that were attached directly to the solid support are transformed into glycosyl donors (see Scheme 1 below).

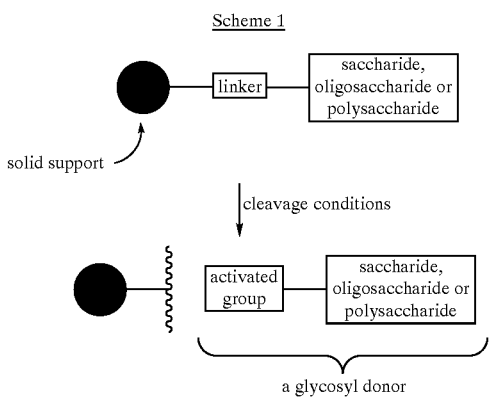

Scheme 1

In certain embodiments, the present invention relates to versatile linkers for tethering a molecule to a solid support, e.g., for tethering a monomer, oligomer or polymer to a solid support, which are stable to a wide range of reaction conditions, but can be cleaved under well-defined conditions, thereby liberating said molecule from the solid support. In preferred embodiments, the linkers of the present invention are used to tether to the solid support unprotected, partially-protected or fully-protected monosaccharides or oligosaccharides, or unprotected, partially-protected or fully-protected glycoconjugates. In other embodiments, the linkers of the present invention may be used to tether to solid supports building blocks useful in the assembly of libraries of other types of small molecules. In certain embodiments, the present invention relates to a molecule or plurality of molecules tethered to the solid support via a linker or linkers of the present invention.

In certain embodiments, the present invention relates to processes for synthesizing molecules, e.g., monomers, oligomers or polymers, on a solid support, wherein a starting material in the synthesis of said molecule, intermediates in the synthesis of said molecule, and said molecule itself are tethered to the solid support during the process via one of the linkers of the present invention. In certain processes of the present invention, the molecule is liberated from the solid support by cleavage of the linker of the present invention.

Compounds of the Invention

In certain embodiments, a linker of the present invention are represented by generalized structure 9:

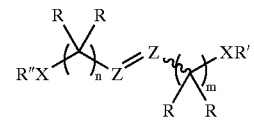

9 wherein
X independently for each occurrence represents O, S, Se, NR, PR or AsR;
Z independently for each occurrence represents CR, SiR, N, P or As;
R independently for each occurrence represents hydrogen, alkyl, aryl or heteroaryl;
R' represents hydrogen or a solid support;
R" represents hydrogen, a mono-, oligo- or polysaccharide, a glycoconjugate, or a small molecule;
n is 3; and
m is an integer greater than or equal to 2.

In certain embodiments, a linker of the present invention is represented by generalized structure 9 and the attendant definitions, wherein X independently for each occurrence represents O, S, or NR.

In certain embodiments, a linker of the present invention is represented by generalized structure 9 and the attendant definitions, wherein X independently for each occurrence represents O.

In certain embodiments, a linker of the present invention is represented by generalized structure 9 and the attendant definitions, wherein Z independently for each occurrence represents CR or N.

In certain embodiments, a linker of the present invention is represented by generalized structure 9 and the attendant definitions, wherein Z independently for each occurrence represents CR.

In certain embodiments, a linker of the present invention is represented by generalized structure 9 and the attendant definitions, wherein X independently for each occurrence represents O, S, or NR; and Z independently for each occurrence represents CR or N.

In certain embodiments, a linker of the present invention is represented by generalized structure 9 and the attendant definitions, wherein X independently for each occurrence represents O; and Z independently for each occurrence represents CR or N.

In certain embodiments, a linker of the present invention is represented by generalized structure 9 and the attendant definitions, wherein X independently for each occurrence represents O; and Z independently for each occurrence represents CR.

In certain embodiments, a linker of the present invention is represented by generalized structure 9 and the attendant definitions, wherein R independently for each occurrence represents hydrogen or alkyl.

In certain embodiments, a linker of the present invention is represented by generalized structure 9 and the attendant definitions, wherein X independently for each occurrence represents O, S, or NR; and R independently for each occurrence represents hydrogen or alkyl.

In certain embodiments, a linker of the present invention is represented by generalized structure 9 and the attendant definitions, wherein X independently for each occurrence represents O; and R independently for each occurrence represents hydrogen or alkyl.

In certain embodiments, a linker of the present invention is represented by generalized structure 9 and the attendant definitions, wherein Z independently for each occurrence represents CR or N; and R independently for each occurrence represents hydrogen or alkyl.

In certain embodiments, a linker of the present invention is represented by generalized structure 9 and the attendant definitions, wherein Z independently for each occurrence represents CR; and R independently for each occurrence represents hydrogen or alkyl.

In certain embodiments, a linker of the present invention is represented by generalized structure 9 and the attendant definitions, wherein X independently for each occurrence represents O, S, or NR; Z independently for each occurrence represents CR or N; and R independently for each occurrence represents hydrogen or alkyl.

In certain embodiments, a linker of the present invention is represented by generalized structure 9 and the attendant definitions, wherein X independently for each occurrence represents O; Z independently for each occurrence represents CR or N; and R independently for each occurrence represents hydrogen or alkyl.

In certain embodiments, a linker of the present invention is represented by generalized structure 9 and the attendant definitions, wherein X independently for each occurrence represents O; Z independently for each occurrence represents CR; and R independently for each occurrence represents hydrogen or alkyl.

In certain embodiments, a linker of the present invention is represented by generalized structure 9 and the attendant definitions, wherein R' represents a solid support.

In certain embodiments, a linker of the present invention is represented by generalized structure 9 and the attendant definitions, wherein R' represents H.

In certain embodiments, a linker of the present invention is represented by generalized structure 9 and the attendant definitions, wherein R" represents H.

In certain embodiments, a linker of the present invention is represented by generalized structure 9 and the attendant definitions, wherein R" represents a monosaccharide or oligosaccharide.

In certain embodiments, a linker of the present invention is represented by generalized structure 9 and the attendant definitions, wherein R" represents a monosaccharide, wherein the anomeric carbon of said monosaccharide is bonded to X.

In certain embodiments, a linker of the present invention is represented by generalized structure 9 and the attendant definitions, wherein R" represents an oligosaccharide, wherein an anomeric carbon of said oligosaccharide is bonded to X.

In certain embodiments, a linker of the present invention is represented by generalized structure 9 and the attendant definitions, wherein R' represents a solid support; and R" represents H.

In certain embodiments, a linker of the present invention is represented by generalized structure 10:

10 wherein
X independently for each occurrence represents O, S, Se, NR, PR or AsR;

R independently for each occurrence represents hydrogen, alkyl, aryl or heteroaryl;

R' represents hydrogen or a solid support;

R" represents hydrogen, a mono-, oligo- or polysaccharide, a glycoconjugate, or a small molecule;

n is 3; and m is an integer greater than or equal 2.

In certain embodiments, a linker of the present invention is represented by generalized structure 10 and the attendant definitions, wherein X independently for each occurrence represents O, S, or NR.

In certain embodiments, a linker of the present invention is represented by generalized structure 10 and the attendant definitions, wherein X independently for each occurrence represents O.

In certain embodiments, a linker of the present invention is represented by generalized structure 10 and the attendant definitions, wherein R independently for each occurrence represents hydrogen or alkyl.

In certain embodiments, a linker of the present invention is represented by generalized structure 10 and the attendant definitions, wherein X independently for each occurrence represents O, S, or NR; and R independently for each occurrence represents hydrogen or alkyl.

In certain embodiments, a linker of the present invention is represented by generalized structure 10 and the attendant definitions, wherein X independently for each occurrence represents O; and R independently for each occurrence represents hydrogen or alkyl.

In certain embodiments, a linker of the present invention is represented by generalized structure 10 and the attendant definitions, wherein R' represents a solid support.

In certain embodiments, a linker of the present invention is represented by generalized structure 10 and the attendant definitions, wherein R' represents H.

In certain embodiments, a linker of the present invention is represented by generalized structure 10 and the attendant definitions, wherein R" represents H.

In certain embodiments, a linker of the present invention is represented by generalized structure 10 and the attendant definitions, wherein R" represents a monosaccharide or oligosaccharide.

In certain embodiments, a linker of the present invention is represented by generalized structure 10 and the attendant definitions, wherein R" represents a monosaccharide, wherein the anomeric carbon of said monosaccharide is bonded to X.

In certain embodiments, a linker of the present invention is represented by generalized structure 10 and the attendant definitions, wherein R" represents an oligosaccharide, wherein an anomeric carbon of said oligosaccharide is bonded to X.

In certain embodiments, a linker of the present invention is represented by generalized structure 10 and the attendant definitions, wherein R' represents a solid support; and R" represents H.

In certain embodiments, a linker of the present invention is represented by generalized structure 11:

11 wherein
X independently for each occurrence represents O, S, Se, NR, PR or AsR;

R independently for each occurrence represents hydrogen, alkyl, aryl or heteroaryl;

R' represents hydrogen or a solid support;

R" represents hydrogen, a mono-, oligo- or polysaccharide, a glycoconjugate, or a small molecule;

n is 3; and m is an integer greater than or equal 2.

In certain embodiments, a linker of the present invention is represented by generalized structure 11 and the attendant definitions, wherein X independently for each occurrence represents O, S, or NR.

In certain embodiments, a linker of the present invention is represented by generalized structure 11 and the attendant definitions, wherein X independently for each occurrence represents O.

In certain embodiments, a linker of the present invention is represented by generalized structure 11 and the attendant definitions, wherein R independently for each occurrence represents hydrogen or alkyl.

In certain embodiments, a linker of the present invention is represented by generalized structure 11 and the attendant definitions, wherein X independently for each occurrence represents O, S, or NR; and R independently for each occurrence represents hydrogen or alkyl.

In certain embodiments, a linker of the present invention is represented by generalized structure 11 and the attendant definitions, wherein X independently for each occurrence represents O; and R independently for each occurrence represents hydrogen or alkyl.

In certain embodiments, a linker of the present invention is represented by generalized structure 11 and the attendant definitions, wherein R' represents a solid support.

In certain embodiments, a linker of the present invention is represented by generalized structure 11 and the attendant definitions, wherein R' represents H.

In certain embodiments, a linker of the present invention is represented by generalized structure 11 and the attendant definitions, wherein R" represents H.

In certain embodiments, a linker of the present invention is represented by generalized structure 11 and the attendant definitions, wherein R" represents a monosaccharide or oligosaccharide.

In certain embodiments, a linker of the present invention is represented by generalized structure 11 and the attendant definitions, wherein R" represents a monosaccharide, wherein the anomeric carbon of said monosaccharide is bonded to X.

In certain embodiments, a linker of the present invention is represented by generalized structure 11 and the attendant definitions, wherein R" represents an oligosaccharide, wherein an anomeric carbon of said oligosaccharide is bonded to X.

In certain embodiments, a linker of the present invention is represented by generalized structure 11 and the attendant definitions, wherein R' represents a solid support; and R" represents H.

In certain embodiments, a linker of the present invention is represented by generalized structure 11 and the attendant definitions, wherein R' represents a solid support; and R" represents a monosaccharide or oligosaccharide.

Processes of the Invention

In certain embodiments, the present invention relates to a process of synthesis, comprising the step of:

reacting a linker represented by generalized structure 9, 10 or 11, wherein R' represents a solid support, with a compound to give a linker represented by generalized structure 9, 10 or 11, wherein R' represents a solid support, and R" comprises said compound.

In certain embodiments, the present invention relates to a process of synthesis, comprising the step of:

reacting a linker represented by generalized structure 9, 10 or 11, wherein R' represents a solid support, with a compound, wherein said compound is a monosaccharide or oligosaccharide, to give a linker represented by generalized structure 9, 10 or 11, wherein R' represents a solid support, and R" comprises said compound.

In certain embodiments, the present invention relates to a process of synthesis, comprising the steps of:

reacting a linker represented by generalized structure 9, 10 or 11, wherein R' represents a solid support, with a compound to give a linker represented by generalized structure 9, 10 or 11, wherein R' represents a solid support, and R" comprises said compound; and cleaving said linker to give a product that is not tethered to a solid support.

In certain embodiments, the present invention relates to a process of synthesis, comprising the steps of:

reacting a linker represented by generalized structure 9, 10 or 11, wherein R' represents a solid support, with a compound, wherein said compound is a monosaccharide or oligosaccharide, to give a linker represented by generalized structure 9, 10 or 11, wherein R' represents a solid support, and R" comprises said compound; and cleaving said linker to give a product that is not tethered to a solid support, wherein said product is an oligosaccharide.

In certain embodiments, the present invention relates to a process of synthesis, comprising the steps of:

reacting a linker represented by generalized structure 9, 10 or 11, wherein R' represents a solid support, with a compound, wherein said compound is a monosaccharide or oligosaccharide, to give a linker represented by generalized structure 9, 10 or 11, wherein R' represents a solid support, and R" comprises said compound; and cleaving said linker to give a product that is not tethered to a solid support, wherein said product is an oligosaccharide comprising a glycosyl donor.

In certain embodiments, the present invention relates to a process of synthesis, comprising the steps of:

reacting a linker represented by generalized structure 9, 10 or 11, wherein R' represents a solid support, with a compound to give a linker represented by generalized structure 9, 10 or 11, wherein R' represents a solid support, and R" comprises said compound; and cleaving said linker by ozonolysis, olefin metathesis, or oxidation to give a product that is not tethered to a solid support.

In certain embodiments, the present invention relates to a process of synthesis, comprising the steps of:

reacting a linker represented by generalized structure 9, 10 or 11, wherein R' represents a solid support, with a compound, wherein said compound is a monosaccharide or oligosaccharide, to give a linker represented by generalized structure 9, 10 or 11, wherein R' represents a solid support, and R" comprises said compound; and cleaving said linker by ozonolysis, olefin metathesis, or oxidation to give a product that is not tethered to a solid support, wherein said product is an oligosaccharide.

In certain embodiments, the present invention relates to a process of synthesis, comprising the steps of:

reacting a linker represented by generalized structure 9, 10 or 11, wherein R' represents a solid support, with a compound, wherein said compound is a monosaccharide or oligosaccharide, to give a linker represented by generalized structure 9, 10 or 11, wherein R' represents a solid support, and R" comprises said compound; and cleaving said linker by ozonolysis, olefin metathesis, or oxidation to give a product that is not tethered to a solid support, wherein said product is an oligosaccharide comprising a glycosyl donor.

In certain embodiments, the present invention relates to a process of synthesis, comprising the steps of:

reacting a linker represented by generalized structure 9, 10 or 11, wherein R' represents a solid support, with a compound, wherein said compound is a monosaccharide or oligosaccharide, to give a linker represented by generalized structure 9, 10 or 11, wherein R' represents a solid support, and R" comprises said compound; and cleaving said linker by olefin metathesis to give a product that is not tethered to a solid support, wherein said product is an oligosaccharide comprising an n-pentenyl glycoside.

In certain embodiments, the new linkers (see Scheme 2 below) described herein dovetail with the synthetic logic of n-pentenyl glycosides. While the number of atoms between the first saccharide, or other building block, and π-bond of The new linkers are stable to a wide range of reaction conditions, but may be used to generate fully-protected oligosaccharide building blocks as well as a variety of anomeric handles (see Scheme 3 below). Cleavage of the octenediol based linker using olefin metathesis with ethylene in the presence of Grubbs' catalyst provides a pentenyl glycoside which in turn may function as a glycosyl donor. Alternatively, activation of the anomeric position by treatment with NIS/TESOTf or NBS/TESOTf or iodonium collidine perchlorate directly fashions glycosides when alkyl, benzyl or aryl alcohols are used. The double bond can be cleaved to afford a terminal aldehyde by ozonolysis or epoxidation (e.g. MCPBA) and cleavage of the epoxide (e.g. periodinate). Alternatively, dihydroxylation and periodinate cleavage will afford the desired aldehyde. The aldehyde group on the anomeric spacer can be further converted into an alcohol or carboxylic acid functionality. These terminal groups will be exploited to fashion a range of neoglycoconjugates by reaction with various functional groups, e.g., alcohols, amines or carboxylic acids.

Scheme 3
A new linker for solid support oligosaccharide synthesis.

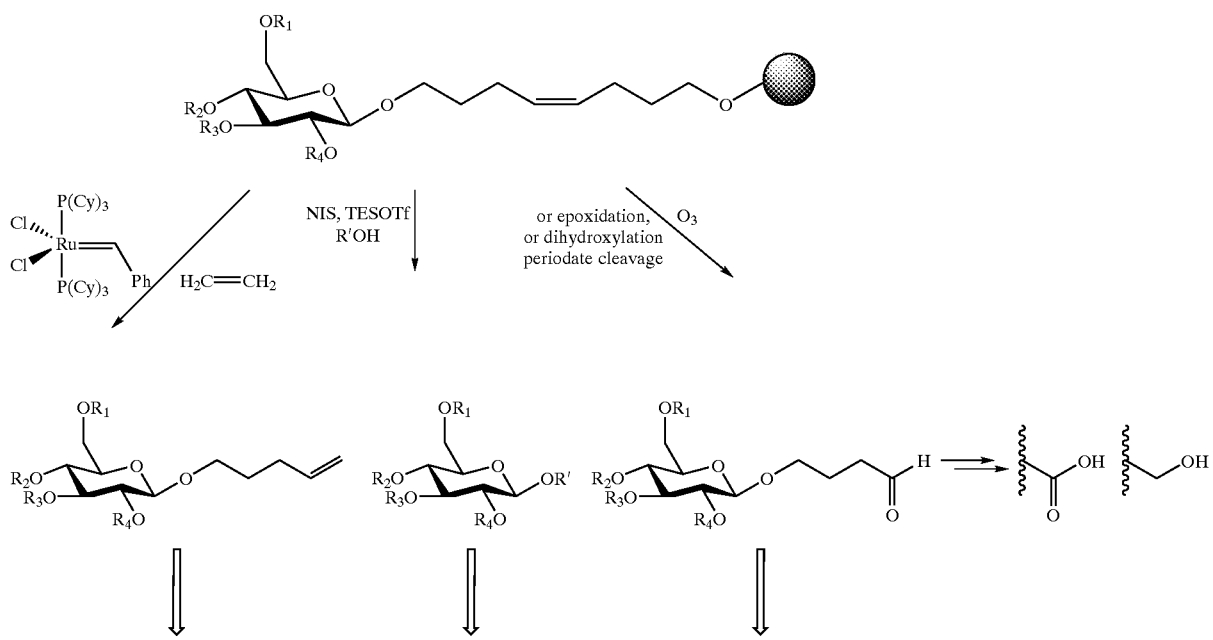

the linker is fixed (n=3), to allow for the release of a pentenyl glycoside, or its equivalent, from the solid support, the number of atoms (m) between the π-bond and the resin may be greater than or equal to 2. The resin attached to the linker and represented by the filled circle may be of any type known to those of ordinary skill in the art, e.g., polystyrene.

Scheme 2
Structure of the novel linker.

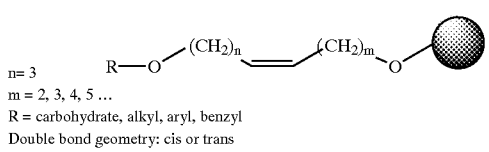

n = 3
m = 2, 3, 4, 5 ...
R = carbohydrate, alkyl, aryl, benzyl
Double bond geometry: cis or trans The use of metathesis reactions to effect the cleavage of a linker from the solid support can be extended to a design which allows for a ring closing metathesis reaction for cleavage (see Scheme 4 below). This design does not require the presence of ethylene for cleavage. Nicolaou et al. have used ring closing metathesis for release of a support-bound molecule wherein the metathesis reaction formed a new ring in the molecule released. Nicolaou, K. C.; Winssinger, N.; Pastor, J.; Ninkovic, S.; Sarabia, F.; He, Y.; Vourloumis, D.; Yang, Z.; Li, T.; Giannakakou, P.; Hamel, E. *Nature* 1997, 387, 268. In our design, the metathesis reaction releases a pentenyl glycoside and the new ring will be formed within the portion of the linker that remains attached to the solid support.

Scheme 4
Linker concept using ring closing metathesis for release of the oligosaccharide.

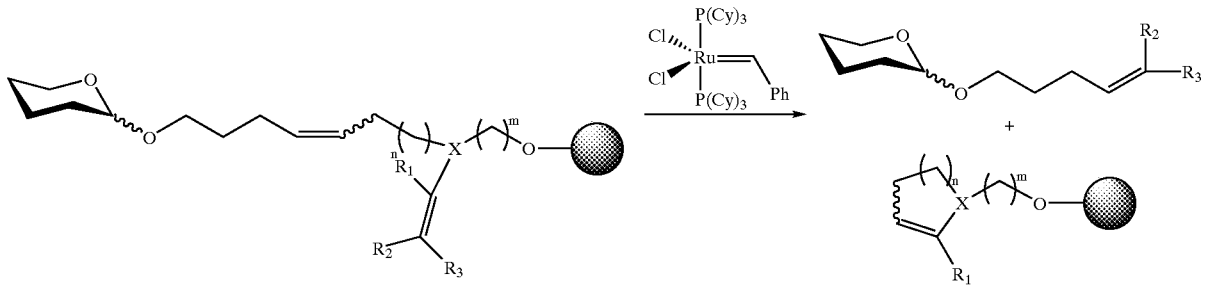

n = 1, 2, 3, ...
m = 1, 2, 3...
$R_1$ = H, alkyl
$R_2$ = H, alkyl
$R_3$ = H, alkyl
X = alkyl, aryl The linkers have been rendered inert to a wide variety of reagents which react with double bonds by their bromination using known conditions to form the corresponding dibromide. See, e.g., Fraser-Reid, B.; Udodong, U. E.; Wu, Z.; Ottosson, H.; Merritt, J. R.; Rao, C. S.; Roberts, C.; Madsen, R. *Synlett* 1992, 927. The dibromide has been transformed back to the double bond by treatment with zinc, tetrabutylammonium iodide or samarium (II) iodide (see Scheme 5 below). This modification allows for the use of reagents on the solid phase which would react with the double bond. The brominated linker allows for the use of pentenyl glycosides as glycosylating agents, which can be activated by NIS/TESOTf, and for the use of hydrogenation conditions, e.g., to remove benzyl protecting groups.

This linker has been used in syntheses on solid support of oligosaccharides, employing the most powerful glycosyl donors developed to date, e.g., thioethyl glycosides, glycosyl trichloroacetimidates, glycosyl fluorides, and glycosyl phosphates.

The most popular approach to the solid-phase preparation of oligosaccharides has been the acceptor-bound synthesis strategy, i.e., a strategy in which the glycosyl acceptor is attached to the solid support, typically through the anomeric carbon of the first residue. Utilizing traditional linkers, the acceptor-bound strategy is poorly suited to the preparation of glycoconjugates. The inability to provide efficiently anomeric glycoconjugates, the most common type of glycoconjugate, is a major shortcoming of the acceptor-bound strategy. The proposed pentenyl glycoside linkers allow for direct functionalization of the anomeric position and overcome this problem.

Scheme 5
Modification of the linker.

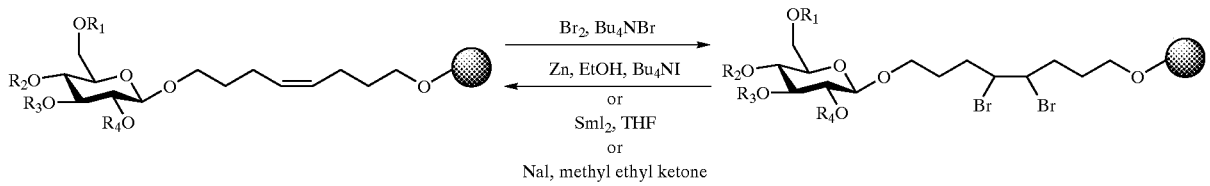

Scheme 6
Solid support synthesis of oligosaccharides using glycosyl phosphates and the novel linker.

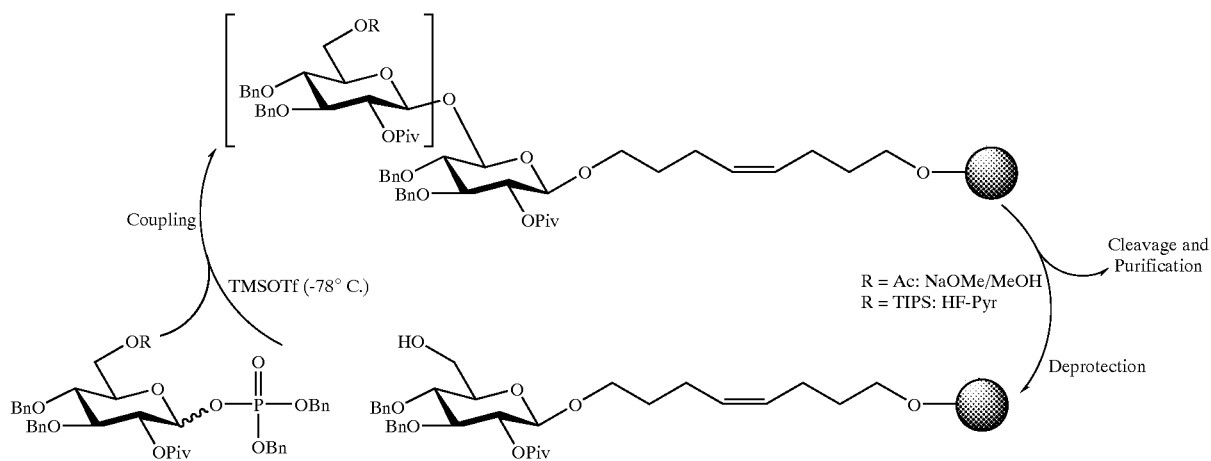

A simple two step coupling cycle has been established (see Scheme 6 above). Removal of a temporary silyl ether or acetate protecting group exposes one hydroxyl group which will serve as a glycosyl acceptor in the next step. Acetate groups are removed by reaction with sodium methoxide while silyl ethers are cleaved by the action of HF-pyridine. Coupling of the incoming monosaccharide donor can be effected by activation with TMSOTf at −78° C. in cases where glycosyl phosphates are employed. Coupling times of less than 30 minutes are expected.

Using the cleavage conditions described above, oligosaccharides containing different anomeric functionalities may be prepared. The functional groups may be exploited to access a host of neoglycoconjugates, dendrimers and other constructs.

The problem of efficiently generating molecular diversity has been tremendously simplified by the advent of combinatorial chemistry. See, e.g., Thompson, L. A.; Ellman, J. A. *Chem. Rev.* 1996, 96, 555–600. This concept when combined with solid-phase synthesis presents a powerful technique for the rapid construction of structurally diverse libraries of compounds which may be screened against therapeutic targets.

The olefinic linker disclosed here can serve as a handle in the preparation of combinatorial libraries of small molecules. Cleavage from the solid support can be accomplished in several ways including acidic hydrolysis, ring-closing metathesis (see, e.g., Maarseveen, J. H. et al. *Tetrahedron Lett.* 1996, 37, 8249–52), ozonolysis, and iodination (see Scheme 3 above). Potential targets include a host of heterocyclic compounds which make up the majority of pharmaceuticals produced today.

The linkers of the present invention provide many advantages over the linkers currently known in the art. Currently available linkers for solid support oligosaccharide synthesis are either so labile that they severely restrict the chemistry on the solid support, or they are so stable that almost all chemistries can be accommodated but the final product cannot be cleaved fully. None of the currently available methods allow for cleavage to fashion different anomeric functionalities. The new linker will be stable to a wide range of reactions, therefore allowing for a variety of chemistries to be used. On the other hand, the linker may be cleaved selective and in quantitative yield at the end of the synthesis.

In addition, a variety of anomeric functionalities may be generated which will serve to access glycoconjugates which may be used as carbohydrate vaccines, targeting devices, molecular probes and many other functions including diagnostics.

Oligosaccharides, either individually or as a library, synthesized utilizing the linkers of the present invention can be used for characterization and elucidation of the biological function(s) of oligosaccharide receptors as well as for the development of clinical diagnostic agents, immunomodulators, therapeutic and conjugate vaccines, and the like. Oligosaccharides prepared utilizing linkers of the present invention will be useful for modulating cell-mediated immune responses in a mammal, including cell-mediated and immune-directed inflammatory responses to an antigen in a sensitized mammal.

Commercial applications of the technology described herein are contemplated. Sales of polymer resins prefunctionalized with various linkers have been booming in the last five years; therefore, the present invention contemplates the development and sale of polymer resins prefunctionalized with linkers of the present invention.

Certain of the oligosaccharides identified by the method of the instant invention will be useful in therapeutic applications for treating or preventing a variety of diseases, including cancer, inflammation, and diseases caused or exacerbated by platelet aggregation or angiogenic activity.

Administration of the oligosaccharides synthesized via the methods of the invention will typically be by routes appropriate for glycosaminoglycan or other carbohydrate compositions, and generally includes systemic administration, such as by injection. For example, intravenous injection, such as continuous injection over long time periods, can be carried out. Also contemplated are introduction into the vascular system through intraluminal administration or by adventitial administration using osmotic pumps or implants. Typical implants contain biodegradable materials such as collagen, polylactate, polylactate/polyglycoside mixtures, and the like. These may be formulated as patches or beads. Typical dosage ranges may be in the range of 0.1–10 mg/kg/hr on a constant basis over a period of 5–30, preferably 7–14, days.

Other modes of administration include subcutaneous injection, including transmembrane or transdermal or other topical administration for localized injury. Localized administration through a continuous release device, such as a supporting matrix, perhaps included in a vascular graft material, can be useful where the location of the trauma is accessible.

Formulations suitable for the foregoing modes of administration are known in the art, and a suitable compendium of formulations is found in Remington's Pharmaceutical Sciences, Mack Publishing Company, Easton, Pa., latest edition.

The oligosaccharides may also be labeled using typical methods such as radiolabeling, fluorescent labeling, chromophores or enzymes, enabling assays of the amount of such compounds in a biological sample following its administration.

Definitions

For convenience, before further description of the present invention, certain terms employed in the specification, examples, and appended claims are collected here.

The term "nucleophile" is recognized in the art, and as used herein means a chemical moiety having a reactive pair of electrons.

The term "electrophile" is art-recognized and refers to chemical moieties which can accept a pair of electrons from a nucleophile as defined above, or from a Lewis base. Electrophilic moieties useful in the method of the present invention include halides and sulfonates.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, ketone, aldehyde, sulfonyl, trifluoromethyl, —CN, chloride, and the like. Exemplary electron-donating groups include amino, methoxy, and the like.

The term "catalytic amount" is recognized in the art and means a substoichiometric amount of a reagent relative to a reactant. As used herein, a catalytic amount means from 0.0001 to 90 mole percent reagent relative to a reactant, more preferably from 0.001 to 50 mole percent, still more preferably from 0.01 to 10 mole percent, and even more preferably from 0.1 to 5 mole percent reagent to reactant.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

The term "arylalkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that comprise a double or triple bond, respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more rings in which two or more carbons are common to two adjoining rings (the rings are "fused") wherein at least one of the rings is aromatic, e.g., the other rings can be cycloalkyls, cycloalkenyls, cycloalkynyls, aryls and/or heterocyclyls.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. Preferred heteroatoms are nitrogen, oxygen, sulfur and phosphorous.

As used herein, the term "nitro" means $-NO_2$; the term "halogen" designates $-F$, $-Cl$, $-Br$ or $-I$; the term "sulfhydryl" means $-SH$; the term "hydroxyl" means $-OH$; and the term "sulfonyl" means $-SO_2-$.

The terms "amine" and "amino" are art recognized and refer to both unsubstituted and substituted amines, e.g., a moiety that can be represented by the general formula:

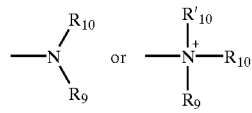

wherein $R_9$, $R_{10}$ and $R'_{10}$ each independently represent a hydrogen, an alkyl, an alkenyl, $-(CH_2)_m-R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or $-(CH_2)_m-R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

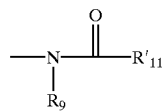

wherein $R_9$ is as defined above, and $R'_{11}$ represents a hydrogen, an alkyl, an alkenyl or $-(CH_2)_m-R_8$, where m and $R_8$ are as defined above.

The term "amido" is art recognized as an amino-substituted carbonyl and includes a moiety that can be represented by the general formula:

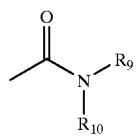

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of $-S$-alkyl, $-S$-alkenyl, $-S$-alkynyl, and $-S-(CH_2)_m-R_8$, wherein m and $R_8$ are defined above. Representative alkylthio groups include methylthio, ethylthio, and the like.

The term "carbonyl" is art recognized and includes such moieties as can be represented by the general formula:

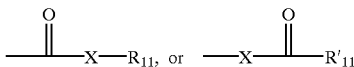

wherein X is a bond or represents an oxygen or a sulfur, and $R_{11}$ represents a hydrogen, an alkyl, an alkenyl, $-(CH_2)_m-R_8$ or a pharmaceutically acceptable salt, $R'_{11}$ represents a hydrogen, an alkyl, an alkenyl or $-(CH_2)_m-R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of $-O$-alkyl, $-O$-alkenyl, $-O$-alkynyl, $-O-(CH_2)_m-R_8$, where m and $R_8$ are described above.

The term "sulfonate" is art recognized and includes a moiety that can be represented by the general formula:

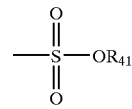

in which $R_{41}$ is an electron pair, hydrogen, alkyl, cycloalkyl, or aryl.

The term "sulfate" is art recognized and includes a moiety that can be represented by the general formula:

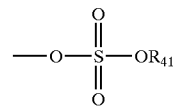

in which $R_{41}$ is as defined above.

The term "sulfonamido" is art recognized and includes a moiety that can be represented by the general formula:

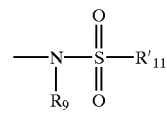

in which $R_9$ and $R'_{11}$ are as defined above.

The term "sulfamoyl" is art-recognized and includes a moiety that can be represented by the general formula:

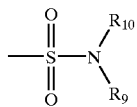

in which $R_9$ and $R_{10}$ are as defined above.

The terms "sulfoxido" or "sulfinyl", as used herein, refers to a moiety that can be represented by the general formula:

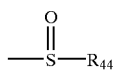

in which $R_{44}$ is selected from the group consisting of hydrogen, alkyl, alkenyl, alkynyl, cycloalkyl, heterocyclyl, aralkyl, or aryl.

A "phosphoryl" can in general be represented by the formula:

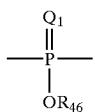

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

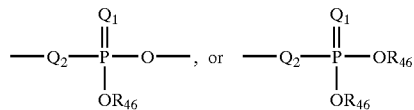

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" can be represented in the general formula:

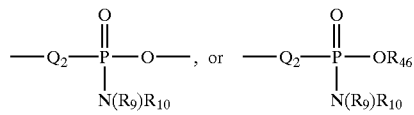

wherein $R_9$ and $R_{10}$ are as defined above, and $Q_2$ represents O, S or N.

A "phosphonamidite" can be represented in the general formula:

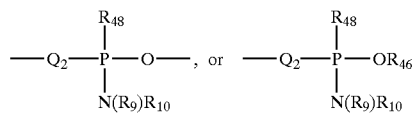

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The abbreviations Me, Et, Ph, Tf, Nf, Ts, Ms, and dba represent methyl, ethyl, phenyl, trifluoromethanesulfonyl, nonafluorobutanesulfonyl, p-toluenesulfonyl, methanesulfonyl, and dibenzylideneacetone, respectively. A more comprehensive list of the abbreviations utilized by organic chemists of ordinary skill in the art appears in the first issue of each volume of the *Journal of Organic Chemistry;* this list is typically presented in a table entitled *Standard List of Abbreviations.* The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The phrase "protecting group" as used herein means temporary modifications of a potentially reactive functional group which protect it from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis,* $2^{nd}$ ed.; Wiley: New York, 1991).

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

A "polar solvent" means a solvent which has a dielectric constant (∈) of 2.9 or greater, such as DMF, THF, ethylene glycol dimethyl ether (DME), DMSO, acetone, acetonitrile, methanol, ethanol, isopropanol, n-propanol, t-butanol or 2-methoxyethyl ether. Preferred solvents are DMF, DME, NMP, and acetonitrile.

A "polar, aprotic solvent" means a polar solvent as defined above which has no available hydrogens to exchange with the compounds of this invention during reaction, for example DMF, acetonitrile, diglyme, DMSO, or THF.

An "aprotic solvent" means a non-nucleophilic solvent having a boiling point range above ambient temperature, preferably from about 25° C. to about 190° C., more preferably from about 80° C. to about 160° C., most preferably from about 80° C. to 150° C., at atmospheric pressure. Examples of such solvents are acetonitrile, toluene, DMF, diglyme, THF or DMSO.

For purposes of this invention, the chemical elements are identified in accordance with the Periodic Table of the Elements, CAS version, Handbook of Chemistry and Physics, 67th Ed., 1986–87, inside cover.

Pharmaceutical Compositions of Compounds Prepared Using Processes of the Present Invention In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and. dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject co,pounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intravectally, for example, as a pessary, cream or foam.

The compounds according to the invention may be formulated for administration in any convenient way for use in human or veterinary medicine, by analogy with other pharmaceuticals.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., San Francisco, U.S.A., 1969 or "Livestock Feeds and Feeding" O and B books, Corvallis, Oreg., U.S.A., 1977).

Overview of Strategies and Methods of Combinatorial Chemistry

In the current era of drug development, high throughput screening of thousands to millions of compounds plays a key role. High throughput screening generally incorporates automation and robotics to enable testing these thousands to millions of compounds in one or more bioassays in a relatively short period of time. This high capacity screening technique requires enormous amounts of "raw materials" having immense molecular diversity to fill available capacity. Accordingly, combinatorial chemistry will play a significant role in meeting this demand for new molecules for screening. Once "leads" are identified using high throughput screening techniques, combinatorial chemistry will be advantageously used to optimize these initial leads (which analogs/variants will be tested in the same high throughput screening assay(s) that identified the initial lead).

A combinatorial library for the purposes of the present invention is a mixture of chemically-related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; Chen et al. (1994) JACS 116:2661: Kerr et al. (1993) JACS 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A) Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) *PNAS* 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811–5814; Valerio et al. (1991) *Anal Biochem* 197:168–177; Bray et al. (1991) *Tetrahedron Lett* 32:6163–6166).

C) Divide-Couple-Recombine

In yet another embodiment, a variegated library of compounds can be provided on a set of beads utilizing the strategy of divide-couple-recombine (see, e.g., Houghten (1985) *PNAS* 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271–280; Fodor, S. P. A. (1991) *Science* 251:767; Pirrung et al. (1992) U.S. Pat. No. 5,143,854; Jacobs et al. (1994) *Trends Biotechnol* 12:19–26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-oligomers

The principle of using oligonucleotides to encode combinatorial synthetic libraries was described in 1992 (Brenner et al. (1992) *PNAS* 89:5381–5383), and an example of such a library appeared the following year (Needles et al. (1993) *PNAS* 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In certain embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529–2531), orthogonality in synthesis is achieved by employing acid-labile protection for the coding strand and base-labile protection for the compound strand.

In an alternative approach (Nikolaiev et al. (1993) *Pept Res* 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-sequenceable Tagging: Binary Encoding

An alternative form of encoding the test compound library employs a set of non-sequencable electrophoric tagging molecules that are used as a binary code (Ohlmeyer et al. (1993) *PNAS* 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

Incorporation by Reference

All of the patents and publications cited herein are hereby incorporated by reference.

Exemplification

The invention may be further understood with reference to the following examples, which are presented for illustrative purposes only and which are non-limiting.

General Experimental Methods Used in the Examples.

Chemicals used were reagent grade and used as supplied by the manufacturer or supplier except where noted. Dichloromethane ($CH_2Cl_2$) was distilled from calcium hydride under $N_2$. Analytical thin-layer chromatography was performed on Merck silica gel 60 $F_{254}$ plates (0.25 mm). Compounds were visualized by dipping the plates in a cerium sulfate-ammonium molybdate solution followed by heating. Liquid column chromatography was performed using forced flow of the indicated solvent on Sigma H-type silica (10–40 μm). $^1H$ NMR spectra were obtained on a Varian VXR-500 (500 MHz) or (300 MHz) and are reported in parts per million (δ) relative to tetramethylsilane (0.00 ppm) or CHCl$_3$ (7.24 ppm). Coupling constants (J) are reported in Hertz. $^{13}$C NMR spectra were obtained on a VXR-500 (125 MHz) and are reported in δ relative to CDCl$_3$ (77.0 ppm) as an internal reference. Polymer bound compounds were analyzed by magic angle spinning NMR with the following conditions: spectra were obtained on a Bruker DRX500 spectrometer, operating at 500.13 MHz ($^1$H) equipped with a 4 mm Bruker CCA HR-MAS probe. Samples 3–6 (20 mg at 0.50 mmol/g) were loaded into a ceramic rotor, suspended in 30 μL CD$_2$Cl$_2$ and spun at the magic angle at 3.5 KHz. $^1$H NMR spectra were obtained with a Carr-Purcell-Meiboom-Gill pulse sequence;128 transients (64 s acquisition time, 0.5 s realization delay) were accumulated.

EXAMPLE 1

Synthesis of (Z)-oct-4-ene-1,8-diol (1) (See FIG. 1)

A solution of 1,5-cyclooctadiene (88.2 g, 0.815 mol) in 500 mL CH$_2$Cl$_2$/MeOH (3:2) was ozonized at −78° C. for 4 h at a rate of 3.3 mmol ozone/min. This solution was then added batchwise to a solution of NaBH$_4$ (30 g, 0.815 mol) in MeOH (2 L) with constant stirring at 0° C. The reaction was warmed to room temperature over the course of 4–5 h and stirred an additional 12 h. The reaction was quenched with 100 mL of 10:1 (H$_2$O/glacial AcOH) and concentrated under vacuum. The aqueous phase was extracted several times with hexanes to remove impurities. The aqueous phase was then extracted with diethyl ether and methylene chloride. The combined organics were dried over Na$_2$SO$_4$, concentrated, and co-evaporated with toluene (3×20 mL) to afford pure diol (50.2 g, 59% yield).

EXAMPLE 2

Synthesis of 4,4'Dimethoxytrityl Functionalized Linker (2) (See FIG. 1)

To a solution of (Z)-oct-4-en-1,8-diol 1 (3.12 g, 21.6 mmol, 3.0 equiv) in pyridine (50 mL) at 0° C. was added 4,4'-dimethoxytrityl chloride (2.44 g, 7.2 mmol, 1.0 equiv). The reaction was gradually warmed to room temperature over 3 h and stirred for an addional 12 h. Ethyl acetate (150 mL) was added and the organics were washed with 100 mL each: H$_2$O, saturated aqueous NaHCO$_3$, brine and H$_2$O; dried over Na$_2$SO$_4$, filtered and concentrated. Purification by flash silica column chromatography (20–50% EtOAc/Hexanes, 1% TEA) afforded 2.513 g 2 (80% based on DMTCl).

EXAMPLE 3

Synthesis of Linker Functionalized Resin (3) (See FIG. 1)

4,4' Dimethoxytrityl functionalized linker 2 (1.391 g, 3.20 mmol, 3.3 equiv) was dissolved in N,N-dimethylformamide (10 mL) and transferred to a solid-phase flask. Upon cooling to 0° C., 60% NaH in mineral oil (0.160 g, 3.20 mmol, 3.3 equiv) were added and the solution was stirred for 1 h. Merrifield's resin (1% crosslinked: 0.800 g, 0.960 mmol, 1.0 equiv) was added along with tetrabutylammonium iodide (35.5 mg, 0.096 mmol, 0.1 equiv). After shaking for 1 h at 0° C., the reaction was warmed to room temperature for 12 h. Capping of unreacted sites was accomplished by reaction with methanol (0.10 mL) and NaH (0.10 g) for 4 h. Methanol (5 mL) was added and the resin was washed with 10 mL each: 1:1 MeOH:DMF, DMF, 3×THF and 3×CH$_2$Cl$_2$. Drying under vacuum over P$_2$O$_5$ afforded 1.077 g resin. Analysis of a small sample of resin (10 mg) via a standard dimethoxytrityl cation assay revealed the loading to be 0.55 mmol/g. Deprotection of the DMT functionalized resin was accomplished by washing the resin with 3×20 mL 3% dichloroacetic acid/CH$_2$Cl$_2$. Further washing with 3×20 mL CH$_2$Cl$_2$, 1% TEA/CH$_2$Cl$_2$, CH$_2$Cl$_2$ and drying under vacuum afforded 0.945 g resin 3 (0.62 mmol/g).

EXAMPLE 4

Synthesis of Resin Bound 6-O-acetyl-3,4-di-O-benzyl-2-O-pivaloyl-β-D-glucopyranoside (4) (See FIG. 1)

Linker functionalized resin 3 (0.2324 g, 0.125 mmol, 1 equiv) was swelled in CH$_2$Cl$_2$ (5 mL) with constant shaking for 15 min. A solution of dibutyl 6-O-acetyl-3,4-di-O-benzyl-2-O-pivaloyl-β-D-glucopyranoside phosphate (0.339 g, 0.500 mmol, 4 equiv) in CH$_2$Cl$_2$ (1 mL) was added via cannula and the reaction vessel was shaken at room temperature for 15 min. After cooling to −78° C. for 30 min, trimethylsilyl triflate (0.101 mL, 0.550 mmol, 4.4 equiv) was added. The reaction was shaken at −78° C. for 1 h then warmed to −65° C. for an additional 2 h. Methanol (10 mL) was added and the resin was washed with 3×10 mL MeOH, THF and CH$_2$Cl$_2$. Drying under vacuum over P$_2$O$_5$ afforded 0.2989 g resin 4.

EXAMPLE 5

Synthesis of Resin Bound 3,4-di-O-benzyl-2-O-pivaloyl-6-O-triisopropylsilyl-β-D-glucopyranoside (5) (See FIG. 1)

Linker functionalized resin 3 (0.500 g, 0.31 mmol, 1 equiv) was swelled in CH$_2$Cl$_2$ (10 mL) with constant shaking for 15 min. A solution of dibutyl 3,4-di-O-benzyl-2-O-pivaloyl-6-O-triisopropylsilyl-β-D-glucopyranoside phosphate (1.03 g, 1.30 mmol, 4 equiv) in CH$_2$Cl$_2$ (3 mL) was added via cannula and the reaction vessel was shaken at room temperature for 30 min. After cooling to −78° C. for 30 min, trimethylsilyl triflate (0.101 mL, 0.550 mmol, 4.4 equiv) in CH$_2$Cl$_2$ (2 mL) was added. The reaction was shaken at −78° C. for 2 h. Methanol (5 mL) was added and the resin was washed with 3×10 mL MeOH, THF and CH$_2$Cl$_2$. Drying under vacuum over P$_2$O$_5$ afforded 0.631 g resin 5.

EXAMPLE 6

Synthesis of resin bound 2-O-acetyl-3,4,6-tri-O-benzyl-α-D-mannopyranoside (6) (See FIG. 1)

Linker functionalized resin 3 (0.489 g, 0.24 mmol, 1.0 equiv) was swelled in a solution of 2-O-acetyl-3,4,6-tri-O-benzyl-α-D-mannopyranosyl trichloroacetimidate (0.623 g, 0.978 mmol) in CH$_2$Cl$_2$ (10 mL) and shaken for 15 min at room temperature. Trimethylsilyltriflate (50 μL, 0.245 mmol) was then added, and the reaction was shaken for 1.5 hr at room temperature. The reaction was then filtered and washed several times switching between CH$_2$Cl$_2$ and THF (10 mL each). Drying under vacuum over P$_2$O$_5$ afforded 0.610 g resin.

EXAMPLE 7

Linker Cleavage via Olefin Metathesis: Preparation of 7 (See FIG. 1)

Monosaccharide functionalized resin 5 (31.1 mg, 0.0146 mmol) was swelled in CH$_2$Cl$_2$ (1 mL) and purged with ethylene. Grubbs' benzylidene catalyst (0.6 mg, 0.70 μmol) was added and the reaction was stirred for 4 h under 1 atm ethylene. An additional 1.2 mg catalyst was added and the reaction was stirred for 12 h. The suspension was filtered through celite and rinsed extensively with $CH_2Cl_2$. Flash silica column chromatography (7% EtOAc/Hexanes) afforded 7 (4.8 mg, 48% for two steps).

EXAMPLE 8

Linker Cleavage via Ozonolysis: Preparation of 8 (See FIG. 1)

Monosaccharide functionalized resin 6 (179 mg, 0.0895 mmol) was swelled in $CH_2Cl_2$ (10 mL) and cooled to −78° C. Ozone was bubbled through until a blue color persisted. The reaction was purged with oxygen. Triphenylphosphine (77 mg, 0.2685 mmol) was added and the dry ice/acetone bath was removed. The reaction was stirred for 12 h. After concentration, flash silica column chromatography afforded 18 mg 8 (40% for two steps).

EXAMPLE 9

A Novel 4,5-Dibromooctane-1,8-diol Linker for Solid-Phase Oligosaccharide Synthesis A novel 4,5-dibromooctane-1,8-diol linker served in the solid support preparation of a (1→6) trisaccharide employing electrophilic activation of thioethyl glycoside building blocks. Debromination of the resin-bound linker-double bond could effectively be carried out by olefin cross-metathesis revealing the desired trimeric n-pentenyl glycoside. High-resolution Magic Angle Spinning NMR (HR-MAS NMR) spectroscopy was used as an analytical tool for the monitoring and development of the solid-phase reactions.

The importance of oligosaccharides in a multitude of biological processes[1] has sparked the interest of biologists and chemists alike. While the need for chemically defined oligosaccharides has steadily increased in recent years, the synthesis and purification of these molecules remains challenging and is carried out by a few specialized laboratories. Oligonucleotides[2] and oligopeptides[3] are now routinely prepared on automated synthesizers, providing pure substances in a rapid and efficient manner. Solid-phase oligosaccharide synthesis holds the potential to secure the necessary substrates for biochemical and biophysical studies.

A number of different approaches to solid-phase oligosaccharide synthesis involving a variety of glycosylation agents such as sulfoxides,[4] 1,2-anhydrosugars,[5] n-pentenyl glycosides,[6] glycosyl trichloroacetimidates,[7] thioglycosides,[8] and phosphates,[9] have been explored. The connection of the first sugar to the polymeric support via a linker is of crucial importance in terms of the synthetic strategy and ultimately the success of the synthesis. The linker has to be completely stable under the reaction conditions but should be cleavable under selective and mild conditions at the end of the synthesis.

A variety of groups including silanes,[10] thioethers,[8a] benzylidene acetals,[11] succinamides,[12] photolabile esters,[6,8b,13] p-acylaminobenzyl esters,[14] branched alkenes,[15] and tris(alkoxy)benzyl amines (BAL)[16] have been employed to anchor the growing oligosaccharide to the solid support. Most of these linkers interfere with some common activation or deprotection conditions, thus limiting the versatility and flexibility in synthetic planning.

Recently, we introduced a novel linker concept for the solid-support synthesis of oligosaccharides.[9] This 4-octene-1,8-diol (see Scheme 1 below) can be cleaved by olefin cross-metathesis. The linker proved to be acid and base stable, and performed extremely well with glycosyl trichloroacetimidate and glycosyl phosphate building blocks. Two classes of versatile glycosylating agents, thioglycosides[17] and n-pentenyl glycosides[18] (NPG) require strongly electrophilic activators, such as N-iodosuccinimide (NIS) and trimethylsilyl triflate (TMSOTf). These conditions are incompatible with linkers containing olefinic double bonds. A universally applicable linker that is inert to a wide range of glycosylation and deprotection conditions employed in oligosaccharide synthesis would be most useful. Here we introduce a 4,5-dibromooctane-1,8-diol linker that makes the synthetic utility of the octenediol linker concept available to syntheses using NPG and thioglycoside building blocks. A trisaccharide was prepared using a novel dibromomasked octenediol linker.

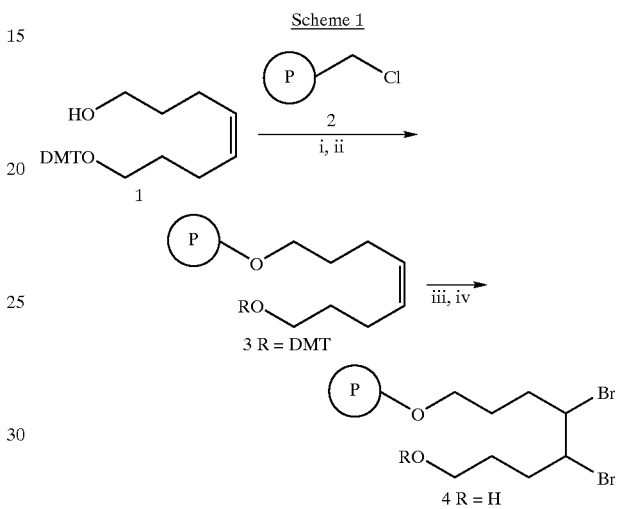

Scheme 1

Synthesis of the dibrominated octane diol linker, P = Merrifield's Resin . i) NaH, DMF ii) NaH, MeOH, iii) LiBr, $CuBr_2$, MeCN, THF, 90% iv) $Cl_2HCCOOH$, $CH_2Cl_2$, 100%.

Initially, a reliable sequence for the installation of the dibromoactanediol (DBOD) linker was developed. Reaction of mono-protected octenediol 1 resulted in efficient functionalization of Merrifield's resin 2 as described previously[9] followed by the capping of unreacted resin with methanol (see Scheme 1 above). Dibromination[19] of linker 3 using $CuBr_2$ and LiBr in acetonitrile/THF, followed by exposure of the free hydroxyl group under acidic conditions proceeded smoothly to furnish resin-bound dibromo octanediol 4. High-resolution magic angle spinning NMR spectroscopy (HR-MAS NMR)[20] indicated complete conversion of the alkene as judged by disappearance of the olefinic proton signals (~5.4 ppm in the $^1$H-NMR; see FIG. 10, spectra a and b).

The stability of the new linker to electrophilic activation was first evaluated using a n-pentenyl mannoside donor (see Scheme 2 below). The resin-bound DBOD linker 4 was reacted with mannosyl donor 5 upon activation by NIS and TMSOTf to produce support-bound monosaccharide 6 in 73% yield.

Scheme 2

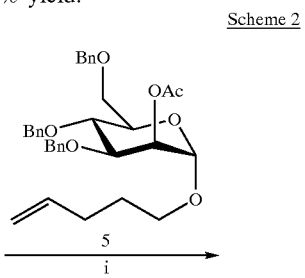

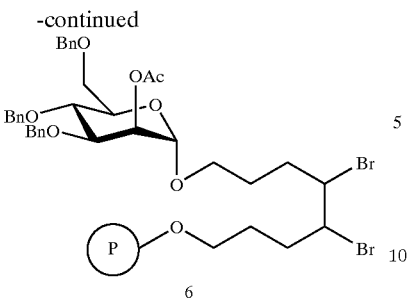

Glycosylation using a n-pentenyl donor. i) NIS, TMSOTf, CH$_2$Cl$_2$, Et$_2$O, 3 h.

Next, the coupling of thioglycoside donors for coupling on the DBOD linker was studied (see Scheme 3 below). Resin-bound acceptor 4 was reacted with thioethyl donor 7 in the presence of NIS and TMSOTf to yield glucoside 8. Deprotection of the 6-O-acetate proceeded smoothly using guanidine in MeOH/THF, to afford acceptor 9.[7c,21] The use of stronger bases such as NaOMe resulted in side products caused by bromide elimination as determined by HR-MAS. The acetates could be removed in the presence of the dibromide by action of hydrogen chloride in 1,4-dioxane/methanol. Iteration of the coupling and deprotection sequence produced trisaccharide 12. All intermediates were examined by HR-MAS to confirm the formation of the desired linkages.

After completion of the desired trisaccharide a two step cleavage protocol was developed. Reductive debromination[22] of the resin-bound linker was achieved with tetrabutylammonium iodide (TBAI) in 4-butanone/1,4-dioxane to yield octenediol-linked trisaccharide 13 as unambiguously confirmed by HR-MAS NMR (see FIG. 10, spectrum c). TBAI was found to perform better in this reaction than sodium iodide due to its considerably higher solubility. Cleavage from the solid support using 20 mol % of Grubbs' catalyst under an atmosphere of ethylene afforded the fully protected n-pentenyl glycoside 14 in 9% overall yield from 3 (77% per step over 9 steps).

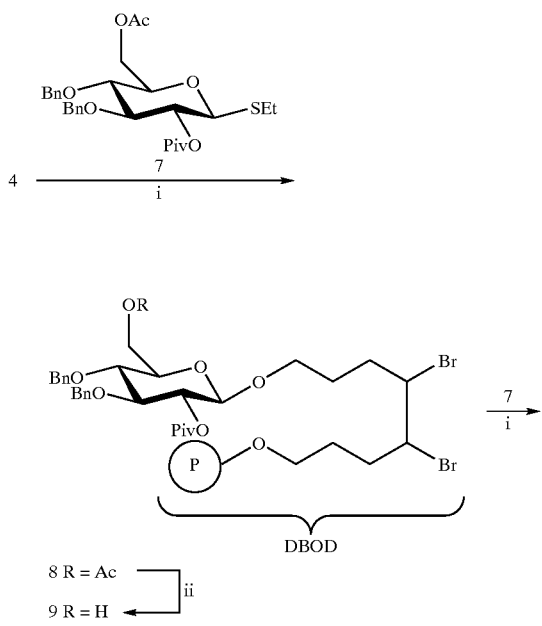

Scheme 3

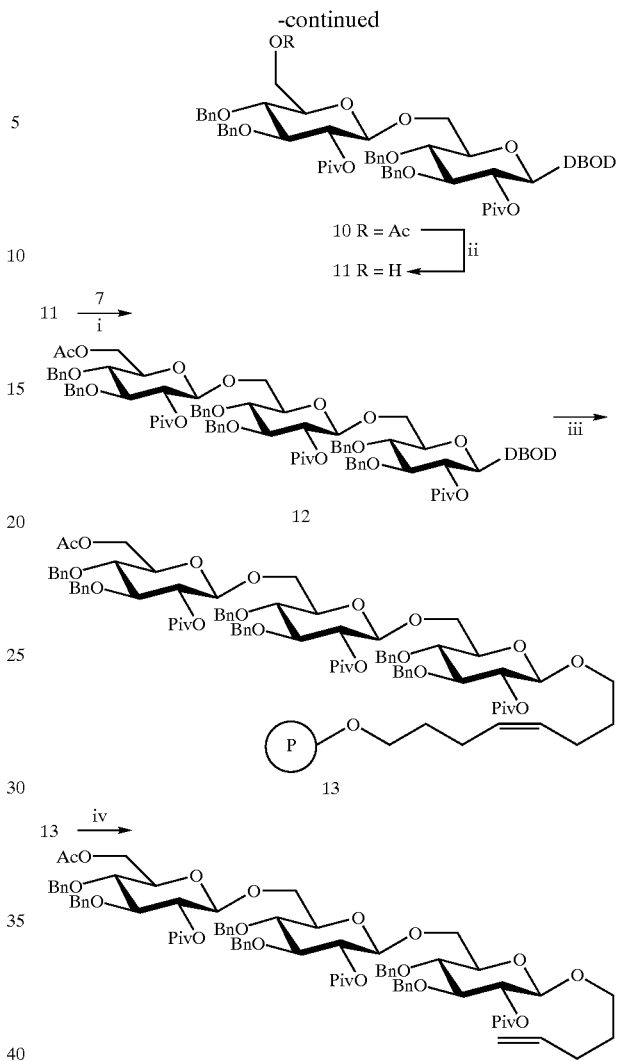

Synthesis of trisaccharide 13 on the DBOD linker.
i) NIS, TMSOTf, CH$_2$Cl$_2$, Et$_2$O, 3 h.
ii) Guanidine, MeOH, THF, 16 h.
iii) TBAI, 4-butanone, 1–4 dioxane, 95° C. 48 h.
iv) Grubbs' catalyst, CH$_2$Cl$_2$, ethylene.

In summary, we have introduced a 4,5-dibromooctane-1,8-diol linker that can be used in solid-phase oligosaccharide synthesis with n-pentenyl glycosides and thioethyl glycosyl donors. This linker, together with the octenediol linker we developed earlier constitutes a universal linker concept compatible with a wide range of activation and deprotection conditions. To demonstrate the utility of the DBOD linker, a trisaccharide was constructed in high yield using thioethyl donors. These studies underscored the value of HR-MAS NMR as a non-destructive analytical tool to the monitor and develop the solid-phase reactions.

Selected Experimental Procedures for Example 9
  a) Bromination of the linker: Functionalized resin 3 (100 mg, 0.065 mmol) was swollen in THF/MeCN. CuBr$_2$ (0.65 mmol) and LiBr (1.3 mmol) were added and the reaction mixture was shaken for 48 h. After being washed the resulting resin was then repeatedly treated with 2% dichloroacetic acid, washed and dried to yield 4.
  b) Glycosylation: Functionalized resin 4 (207 mg, 0.124 mmol) was swollen in CH$_2$Cl$_2$ and activated 4 Å molecular sieves (207 mg) and NIS (1.12 mmol) were added. Thioethyl donor 7 (0.372 mmol) was added as a solution in $CH_2Cl_2$ (2 mL) and the reaction mixture was cooled to 0° C. TMSOTf (0.186 mmol) was added and the reaction shaken for 3 h. The resin was washed and dried to yield monosaccharide 8.

c) Deacetylation: Resin-bound monosaccharide 8 (249 mg, 0.107 mmol) was swollen in THF. Guanidine (1.22 mmol) was added and the reaction shaken for 16 h. The resin was washed and dried to yield monosaccharide acceptor 9. d) Debromination of linker: resin bound trisaccharide 12 (247 mg, 0.084 mmol) was swollen in 4-butanone/1-4 dioxane (2:1, 3 mL). TBAI (2.11 mmol) was added and the reaction was shaken for 48 h at 95° C. The resin was washed with and dried to yield trisaccharide 13.

d) Cleavage from resin: Resin-bound trisaccharide 13 (145 mg, 0.049 mmol) was swollen in $CH_2Cl_2$ Grubbs' catalyst (9.89 μmol) was added and the reaction was stirred for 16 h under an atmosphere of ethylene. Evaporation of the solvent in vacuo followed by silica gel chromatography yielded trisaccharide 14.

References Cited in Example 9
1) Varki, A., *Glycobiology* 1993, 3, 97–130.
2) Caruthers, M. H. *Science* 1985, 230, 281–285.
3) (a) Atherton, E.; Sheppard, R. C. *Solid-phase peptide synthesis: A practical approach;* IRL Press at Oxford University Press: Oxford, England, 1989.
4) Yan, L.; Taylor, C. M.; Goodnow, Jr., R.; Kahne, D. *J. Am. Chem. Soc.* 1994, 116, 6953–6954.
5) Seeberger, P. H.; Danishefsky, S. J. *Acc. Chem. Res.* 1998, 31, 685–695.
6) Rodebaugh, R.; Joshi, S.; Fraser-Reid, B.; Geysen, H. M. *J. Org. Chem.* 1997, 62, 5660–5661.
7) (a) Rademann, J.; Geyer, A.; Schmidt, R. R. *Angew. Chem. Int. Ed.* 1998, 37, 1241–1245. (b) Adinolfi, M.; Barone, G.; De Napoli, L.; Iadonisi, A.; Piccialli, G. *Tetrahedron Lett.* 1998, 39, 1953–1956. (c) Hunt, J. A.; Roush, W. R. *J. Am. Chem. Soc.* 1996, 118, 9998–9999.
8) (a) Zhu, T.; Boons, G.-J. *Angew. Chem. Int. Ed.* 1998, 37, 1898–1900. (b) Nicolaou, K. C.; Watanabe, N.; Li, J.; Pastor, J.; Winssinger, N. *Angew. Chem. Int. Ed.* 1998, 37, 1559–1561. (c) Zheng, C.; Seeberger, P. H.; Danishefsky, S. J. *Angew. Chem. Int. Ed.* 1998, 37, 786–789.
9) Andrade, R. B.; Plante, O. J.; Melean, L. G.; Seeberger, P. H. *Org. Lett.* 1999, 1, 1811–1814.
10) (a) Danishefsky, S. J.; McClure, K. F.; Randolph, J. T.; Ruggeri, R. B. *Science* 1993, 260, 1307–1309. (b) Doi, T.; Sugiki, M.; Yamada, H.; Takahashi, T.; Porco, J. A. Jr. *Tetrahedron Lett.* 1999, 40, 2141–2144.
11) (a) Chiu, S.-H. L.; Anderson, L. *Carbohydr. Res.* 1976, 50, 227. (b) Rademann, J.; Schmidt, R. R. *Tetrahedron Lett.* 1996, 37, 3989–3990.
12) Lampe, T. F. J.; Weitz-Schmidt, G.; Wong, C.-H. *Angew. Chem. Int. Ed.* 1998, 37, 1707–1711.
13) Zehavi, T.; Patchornik, A. *J. Am. Chem. Soc.* 1973, 95, 5673–5677.
14) Fukase, K.; Nakai, Y.; Egusa, K.; Porco, J. A.; Kusumoto, S. *Synlett.* 1999, 7, 1074–1078.
15) Knerr, L.; Schmidt, R. R. *Synlett.* 1999, 11, 1802–1804.
16) Tolborg, J. F.; Jensen, K. J. *Chem. Comm.* 2000, 2, 147–148.
17) Garegg, P. J. *Adv. Carbohydr. Chem. Biochem.,* 1997, 52, 179–205.
18) Fraser-Reid, B.; Udodong, U. E.; Wu, Z.; Ottosson, H.; Merritt, J. R.; Rao, S.; Roberts, C.; Modsen, R. *Synlett* 1992, 922–942.
19) Rodebaugh, R.; Debenham, J. S.; Fraser-Reid, B.; Snyder, J. P. *J. Org. Chem.* 1999, 64, 1758–1761.
20) Seeberger, P. H.; Beebe, X.; Sukenick, G. D.; Pochapsky, S.; Danishefsky, S. J. *Angew. Chem. Int. Ed.* 1997, 36, 491–493.
21) Ellervik, U.; Magnusson, G. *Tetrahedron Lett.* 1997, 38, 1627–1628.
22) Merritt, J. R.; Debenham, J. S.; Fraser-Reid, B. *J. Carbohydr. Chem.* 1996, 15, 65–72.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A compound represented by structure 9:

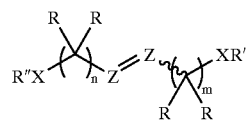

wherein
X independently for each occurrence represents O, S, Se, NR, PR or AsR;
Z independently for each occurrence represents CR, SiR, N, P or As;
R independently for each occurrence represents hydrogen, alkyl, aryl or heteroaryl;
R' represents a solid support;
R" represents hydrogen, a mono-, oligo- or polysaccharide, a glycoconjugate, or a small molecule;
n is 3; and
m is an integer greater than or equal to 2.

2. The compound of claim 1, wherein X independently for each occurrence represents O, S, or NR.

3. The compound of claim 1, wherein X independently for each occurrence represents O.

4. The compound of claim 1, wherein Z independently for each occurrence represents CR or N.

5. The compound of claim 1, wherein Z independently for each occurrence represents CR.

6. The compound of claim 1, wherein X independently for each occurrence represents O, S or NR; and Z independently for each occurrence represents CR or N.

7. The compound of claim 1, wherein X independently for each occurrence represents O; and Z independently for each occurrence represents CR or N.

8. The compound of claim 1, wherein X independently for each occurrence represents O; and Z independently for each occurrence represents CR.

9. The compound of claim 1, wherein R independently for each occurrence represents hydrogen or alkyl.

10. The compound of claim 1, wherein X independently for each occurrence represents O, S, or NR; and R independently for each occurrence represents hydrogen or alkyl.

11. The compound of claim 1, wherein X independently for each occurrence represents O; and R independently for each occurrence represents hydrogen or alkyl.

12. The compound of claim 1, wherein Z independently for each occurrence represents CR or N; and R independently for each occurrence represents hydrogen or alkyl.

13. The compound of claim 1, wherein Z independently for each occurrence represents CR; and R independently for each occurrence represents hydrogen or alkyl.

14. The compound of claim 1, wherein X independently for each occurrence represents O, S, or NR; Z independently for each occurrence represents CR or N; and R independently for each occurrence represents hydrogen or alkyl.

15. The compound of claim 1, wherein X independently for each occurrence represents O; Z independently for each occurrence represents CR or N; and R independently for each occurrence represents hydrogen or alkyl.

16. The compound of claim 1, wherein X independently for each occurrence represents O; Z independently for each occurrence represents CR; and R independently for each occurrence represents hydrogen or alkyl.

17. The compound of claim 1, 2, 3, 4, 5, 6, 7, 8, 9, 10, 11, 12, 13, 14, 15, or 16, wherein R" represents H.

18. A compound represented by structure 10:

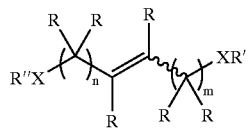

wherein
X independently for each occurrence represents O, S, Se, NR, PR or AsR;

R independently for each occurrence represents hydrogen, alkyl, aryl or heteroaryl;

R' represents a solid support;

R" represents hydrogen, a mono-, oligo- or polysaccharide, a glycoconjugate, or a small molecule;

n is 3; and m is an integer greater than or equal 2.

19. The compound of claim 18, wherein X independently for each occurrence represents O, S, or NR.

20. The compound of claim 18, wherein X independently for each occurrence represents O.

21. The compound of claim 18, wherein R independently for each occurrence represents hydrogen or alkyl.

22. The compound of claim 18, wherein X independently for each occurrence represents O, S, or NR; and R independently for each occurrence represents hydrogen or alkyl.

23. The compound of claim 18, wherein X independently for each occurrence represents O; and R independently for each occurrence represents hydrogen or alkyl.

24. The compound of claim 18, 19, 20, 21, or 23, wherein R" represents H.

* * * * *

UNITED STATES PATENT AND TRADEMARK OFFICE
CERTIFICATE OF CORRECTION

| | | |
|---|---|---|
| PATENT NO. | : 6,579,725 B1 | |
| APPLICATION NO. | : 09/518102 | |
| DATED | : June 17, 2003 | |
| INVENTOR(S) | : Peter H Seeberger | |

It is certified that error appears in the above-identified patent and that said Letters Patent is hereby corrected as shown below:

Add the following Government Support language at column 1, line 9:

-- This invention was made with government support under Grant No. DGE1916148 awarded by the National Science Foundation. The government has certain rights in the invention. --

Signed and Sealed this
Twenty-seventh Day of November, 2012

David J. Kappos
*Director of the United States Patent and Trademark Office*